United States Patent
Sawyer et al.

(10) Patent No.: US 7,411,110 B2
(45) Date of Patent: Aug. 12, 2008

(54) THIN, HIGH CAPACITY ABSORBENT STRUCTURE AND METHOD FOR PRODUCING SAME

(75) Inventors: Lawrence Howell Sawyer, Neenah, WI (US); Michael John Niemeyer, Appleton, WI (US); Lori Tassone Holmes, Neenah, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 723 days.

(21) Appl. No.: 09/939,061

(22) Filed: Aug. 24, 2001

(65) Prior Publication Data

US 2002/0156441 A1 Oct. 24, 2002

Related U.S. Application Data

(60) Provisional application No. 60/257,016, filed on Dec. 20, 2000.

(51) Int. Cl.
*A61F 13/15* (2006.01)
(52) U.S. Cl. ...................... 604/368; 604/374
(58) Field of Classification Search ................ 604/367, 604/368, 374
See application file for complete search history.

(56) References Cited

U.S. PATENT DOCUMENTS

| | | |
|---|---|---|
| 3,494,362 A | 2/1970 | Burgeni |
| 3,849,241 A | 11/1974 | Butin et al. ................. 161/169 |
| 4,610,678 A | 9/1986 | Weisman et al. ............ 604/368 |
| 4,654,039 A | 3/1987 | Brandt et al. |
| 4,663,220 A | 5/1987 | Wisneski et al. ........... 428/221 |
| 4,673,402 A | 6/1987 | Weisman et al. |
| 4,699,823 A * | 10/1987 | Kellenberger et al. ....... 428/219 |
| 4,818,598 A | 4/1989 | Wong ........................ 428/284 |
| 4,940,464 A | 7/1990 | Van Gompel et al. ....... 604/396 |
| 4,950,264 A | 8/1990 | Osborn, III ............... 604/385.1 |
| 5,009,653 A | 4/1991 | Osborn, III ............... 604/385.1 |
| 5,046,272 A | 9/1991 | Vogt et al. .................... 38/143 |
| 5,104,116 A | 4/1992 | Pohjola ..................... 271/185 |
| 5,128,082 A | 7/1992 | Makoui ...................... 264/112 |
| 5,149,335 A | 9/1992 | Kellenberger et al. ....... 604/372 |
| 5,156,902 A | 10/1992 | Pieper et al. |

(Continued)

FOREIGN PATENT DOCUMENTS

EP 122 042 10/1984

(Continued)

OTHER PUBLICATIONS

U.S. Appl. No. 09/475,829, filed Dec. 1998, Dodge, II et al.

(Continued)

*Primary Examiner*—Tatyana Zalukaeva
*Assistant Examiner*—C. Lynne Anderson
(74) *Attorney, Agent, or Firm*—Armstrong Teasdale LLP

(57) ABSTRACT

A thin, flexible, high capacity absorbent pad and a method of making such absorbent pads. The absorbent pad contains high levels of superabsorbent material homogeneously mixed with cellulose pulp fluff. The absorbent pad is subjected to high density compaction to achieve the thinness and high absorbent capacity of the invention. The absorbent pad can be used in absorbent articles, such as diapers, training pants, feminine hygiene products, incontinence products, and swim wear.

44 Claims, 10 Drawing Sheets

U.S. PATENT DOCUMENTS

| | | | |
|---|---|---|---|
| 5,224,405 A | 7/1993 | Pohjola | 83/24 |
| 5,226,992 A | 7/1993 | Morman | 156/62.4 |
| 5,356,403 A * | 10/1994 | Faulks et al. | 604/378 |
| 5,378,528 A | 1/1995 | Makoui | 428/219 |
| 5,451,442 A * | 9/1995 | Pieniak et al. | 428/54 |
| 5,460,622 A | 10/1995 | Dragoo et al. | 604/378 |
| 5,462,537 A * | 10/1995 | Carr et al. | 604/368 |
| 5,466,513 A | 11/1995 | Wanek et al. | 428/218 |
| 5,486,167 A | 1/1996 | Dragoo et al. | 604/384 |
| 5,516,569 A | 5/1996 | Veith et al. | 428/68 |
| 5,547,541 A | 8/1996 | Hansen et al. | 162/12 |
| 5,562,646 A | 10/1996 | Goldman et al. | 604/368 |
| 5,562,793 A | 10/1996 | Menard | |
| 5,601,542 A | 2/1997 | Melius et al. | 604/368 |
| 5,635,239 A | 6/1997 | Chen et al. | 427/180 |
| 5,669,894 A | 9/1997 | Goldman et al. | 604/368 |
| 5,722,967 A * | 3/1998 | Coles | 604/385.04 |
| 5,728,083 A | 3/1998 | Cohen et al. | 604/368 |
| 5,730,737 A | 3/1998 | Widlund et al. | 604/378 |
| 5,762,844 A | 6/1998 | Van Himbergen et al. | |
| 5,827,259 A * | 10/1998 | Laux et al. | 604/385.29 |
| 5,843,063 A | 12/1998 | Anderson et al. | 604/378 |
| 5,866,242 A | 2/1999 | Tan et al. | 428/219 |
| 5,916,670 A | 6/1999 | Tan et al. | 428/219 |
| 5,961,506 A | 10/1999 | Guidotti et al. | 604/378 |
| 6,020,536 A | 2/2000 | Osterdahl et al. | 604/378 |
| 6,037,518 A | 3/2000 | Guidotti et al. | 604/378 |
| 6,060,115 A | 5/2000 | Borowski et al. | 427/200 |
| 6,068,620 A * | 5/2000 | Chmielewski | 604/378 |
| 6,118,042 A | 9/2000 | Palumbo | 604/368 |
| 6,214,274 B1 | 4/2001 | Melius et al. | 264/280 |
| 6,515,195 B1 * | 2/2003 | Lariviere et al. | 604/380 |

FOREIGN PATENT DOCUMENTS

| | | |
|---|---|---|
| EP | 217 032 | 4/1987 |
| EP | 0 292 624 | 11/1988 |
| EP | 325 416 | 7/1989 |
| EP | 0 467 409 A1 | 1/1992 |
| EP | 565 630 | 10/1993 |
| EP | 0 600 454 A1 | 6/1994 |
| EP | 0 627 211 A1 | 12/1994 |
| EP | 737 055 | 10/1996 |
| EP | 898 950 | 3/1999 |
| EP | 0 958 801 A1 | 11/1999 |
| EP | 979 728 | 2/2000 |
| EP | 1 078 616 | 2/2001 |
| GB | 2296510 | 7/1996 |
| GB | 2 306 333 | 5/1997 |
| WO | 95/17870 | 7/1995 |
| WO | 96/11107 | 4/1996 |
| WO | 97/39188 | 10/1997 |
| WO | 98/28479 | 7/1998 |
| WO | WO 99/17695 | 4/1999 |
| WO | 99/25290 | 5/1999 |
| WO | 99/30659 | 6/1999 |
| WO | 00/27625 | 5/2000 |
| WO | WO 02/056812 | 7/2000 |
| WO | WO 00/69383 | 11/2000 |

OTHER PUBLICATIONS

U.S. Patent Application filed on Oct. 23, 2000, by Express Mail No. EL 503 397 837 US ("Forming Media With Enhanced Air Flow Properties").

U.S. Appl. No. 09/475,830, filed Dec. 1998.

* cited by examiner ded to a thin, flexible, high capacity absorbent pad and a method of making such an absorbent pad. The absorbent pad contains high levels of superabsorbent polymer (SAP), homogeneously mixed with cellulose fluff pulp. Alternatively, the SAP can be arranged in a gradient throughout the absorbent pad. The absorbent pad is
THIN, HIGH CAPACITY ABSORBENT STRUCTURE AND METHOD FOR PRODUCING SAME

CROSS REFERENCE TO RELATED APPLICATION

This application claims the benefit of U.S. Provisional Application No. 60/257,016, filed 20 Dec. 2000.

FIELD OF THE INVENTION

This invention is directed to a thin, flexible, high capacity absorbent pad. The absorbent pad can be produced with an online drum former.

BACKGROUND OF THE INVENTION

Many known absorbent composites that include a high-absorbency material include the high-absorbency material in relatively low concentrations. That is, many of the absorbent composites include airlaid cellulosic fibers and less than about 30 weight percent of a high-absorbency material. This is due to several factors.

Many high-absorbency materials are unable to absorb a liquid at a rate at which the liquid is applied to the absorbent composites during use. Accordingly, a relatively high concentration of fibrous material is desirable to temporarily hold the liquid until the high-absorbency material can absorb it. Further, the fibers serve to separate the particles of high-absorbency material so that gel-blocking does not occur. Gel-blocking refers to the situation wherein particles of high-absorbency material deform during swelling and block the interstitial spaces between the particles, or between the particles and the fibers, thus preventing the flow of liquid through the interstitial spaces.

U.S. Pat. No. 5,147,343 issued Sep. 15, 1992, to Kellenberger describes an absorbent composite adapted to avoid the problem of gel-blocking. U.S. Pat. No. 5,147,343 describes the use of a superabsorbent material which can absorb at least 27 milliliters of a 0.9 weight percent aqueous sodium chloride solution per gram of superabsorbent material while the superabsorbent is under a restraining pressure of at least 21,000 dynes per square centimeter. When the superabsorbent material is in the form of discrete particles, at least about 50 percent by weight of the superabsorbent material has a size greater than the median pore size of the porous fiber matrix when wet. The described absorbent composites are said to contain up to about 90 weight percent of a superabsorbent material.

The presence of a relatively low concentration of high-absorbency material and a relatively greater concentration of fibrous materials has resulted in the production of absorbent composites which tend to be relatively thick. In some instances, the use of a relatively thick absorbent composite in a disposable absorbent garment is acceptable. However, in recent years it has become increasingly desirable to produce absorbent composites which are thin compared to the more traditional absorbent composites but which still possess the same absorbent capacity. Thin absorbents provide for a greater garment-like appearance as well as improved discretion when worn under other garments. The desire to produce relatively thin absorbent composites has resulted in the desire to incorporate ever-increasing amounts of high-absorbency material into the absorbent composites. This is because the absorbent capacity of such high-absorbency materials is generally many times greater than the absorbent capacity of fibrous materials. For example, a fibrous matrix of wood pulp fluff can absorb about 7-9 grams of a liquid, (such as 0.9 weight percent saline) per gram of wood pulp fluff, while the high-absorbency materials can absorb at least about 15, preferably at least about 20, and often at least about 25 grams of liquid, such as 0.9 weight percent saline, per gram of the high-absorbency material.

U.S. Pat. No. 5,601,542 issued Feb. 11, 1997, to Melius et al. describes an absorbent composite including a superabsorbent material contained by a containment means. The superabsorbent material has a Pressure Absorbency Index of at least 100 and a 16-hour extractables level of less than about 13 weight percent; a Pressure Absorbency Index of at least 100 and a Vortex Time of less than about 45 seconds; or a Pressure Absorbency Index of at least about 110. The superabsorbent material is present in the containment means in an amount of from about 30 to about 100 weight percent based on the total weight of the containment means and the superabsorbent material.

U.S. Pat. No. 5,149,335 issued Sep. 22, 1992, to Kellenberger et al. is directed to an absorbent structure containing a relatively high concentration of superabsorbent material. Specifically, U.S. Pat. No. 5,149,335 describes the use of a superabsorbent material having certain absorbent characteristics when it is desired to employ the superabsorbent material at relatively high concentrations. Specifically, the superabsorbent material is described as having a 5-minute Absorbency Under Load value of at least about 15 grams per gram and a free-swell rate of less than about 60 seconds.

In striving for thin absorbent composites, other desirable qualities are often sacrificed, such as capacity and flexibility. Quite often, when absorbent pads are densified to create high capacity in a thin form, hard spots develop within the pads, thereby resulting in stiffness and lack of uniformity of the absorbent material within the pads. On the other hand, when thin pads are made having a lower density, the resulting pads may be flexible, but thin, low density pads have a low absorbent capacity. Low density, high capacity pads that are flexible are generally thick and bulky and look and feel cumbersome on the wearer.

Various technologies are known for making absorbent pads. High capacity absorbent pads are typically produced on a conventional absorbent drum former by combining superabsorbent polymer and fluff pulp in a forming chamber. High superabsorbent polymer concentrations and uniform mixing of the absorbent components can lead to superabsorbent polymer containment issues during forming and in the finished product. Superabsorbent polymer loss during pad forming can cause high absorbent variability, inconsistent performance, raw material waste and process upset by loading the recycle system with superabsorbent polymer.

There is thus a need or desire for absorbent pads that are thin, flexible, and have a high absorbent capacity.

There is a further need or desire for a process for making well-mixed, uniform absorbent pads.

There is yet a further need or desire for a process for making absorbent pads in which superabsorbent polymer loss can be minimized.

SUMMARY OF THE INVENTION

The present invention is directed to a thin, flexible, high capacity absorbent pad and a method of making such an absorbent pad. The absorbent pad contains high levels of superabsorbent polymer (SAP), homogeneously mixed with cellulose fluff pulp. Alternatively, the SAP can be arranged in a gradient throughout the absorbent pad. The absorbent pad is subjected to high density compaction to achieve the thin, high capacity absorbent pad of the invention. The absorbent pad is incorporated directly into an absorbent product. The absorbent pad has a thickness between about 0.5 and 3.0 millimeters, and an absorbent capacity, measured using the Saturated Capacity Test at a 0.5 pounds per square inch (psi) load procedure described herein, between about 80 and 800 grams 0.9 w/v % saline solution, available from Ricca Chemical Company of Arlington, Tex. The densified pad exhibits good edge compression properties for user comfort and acceptance. Absorbent performance of the thin, high capacity absorbent pad is comparable to conventional, not-so-thin, low density absorbent pads. Other components can also be added to the absorbent pad, such as man-made fibers, carrier particles, and a variety of chemical additives or treatments.

The thin, high capacity absorbent pad of the invention can be produced on a conventional online absorbent drum former by homogeneously mixing high levels of SAP and fluff pulp in a forming chamber. SAP loss can be minimized by the use of a woven polyester fabric, suitably with about 300 micron pores, wrapped about the forming drum to cover the forming screens. Alternatively, micro-perforated forming screens with openings of approximately 300 microns or smaller may also be used. The openings in the fabric or screens should be small enough to trap most of the SAP particles while leaving enough open area to maintain high enough permeability for pad formation. By using an online drum former, as opposed to an offline former, extra mass and capacity of the absorbent material can be placed in zones where the material is most useful. For example, the pad can be formed to a specific shape, such as hourglass or the like, or extra mass can be positioned in a specific area by creating a deeper pocket in the forming screen. A special SAP dispersion nozzle can be placed in a top front position of the forming chamber to achieve homogeneously mixed SAP and fluff pulp. The pad may be placed on a carrier or wrap tissue or similar material. When the absorbent pad is formed, it leaves the forming chamber at a low density and must then be densified. The densification can be accomplished with a conventional compaction roll or with a heated nip. Humidification of the composite may improve densification and help provide lower edge compression or stiffness values. Use of an embossing pattern may also reduce stiffness.

With the foregoing in mind, it is a feature and advantage of the invention to provide a thin, flexible, high capacity absorbent pad. It is another feature and advantage of the invention to provide a method of making a well-mixed, uniform absorbent pad in which superabsorbent polymer loss can be minimized.

DEFINITIONS

Within the context of this specification, each term or phrase below will include the following meaning or meanings.

"Drum former" is equipment used to produce absorbent pads including a rotating drum supporting a foraminous membrane through which air is pulled from a vacuum source. Raw materials such as pulp fiber, SAP and other components are directed onto the foraminous surface through the air flow.

"Gradient" refers to a graded change in the magnitude of a physical quantity, such as the quantity of superabsorbent present in various locations of an absorbent pad, or other pad characteristics such as mass, density, or the like.

"High gel strength" refers to a material having a gel strength value greater than 0.65, suitably greater than 0.75, or suitably greater than 0.85, wherein gel strength is determined by dividing 0.9 AUL capacity by centrifuge retention capacity (CRC).

"Homogeneously mixed" refers to the uniform mixing of two or more substances within a composition, such that the magnitude of a physical quantity of each of the substances remains substantially consistent throughout the composition.

"Layer" when used in the singular can have the dual meaning of a single element or a plurality of elements.

Figure 2:
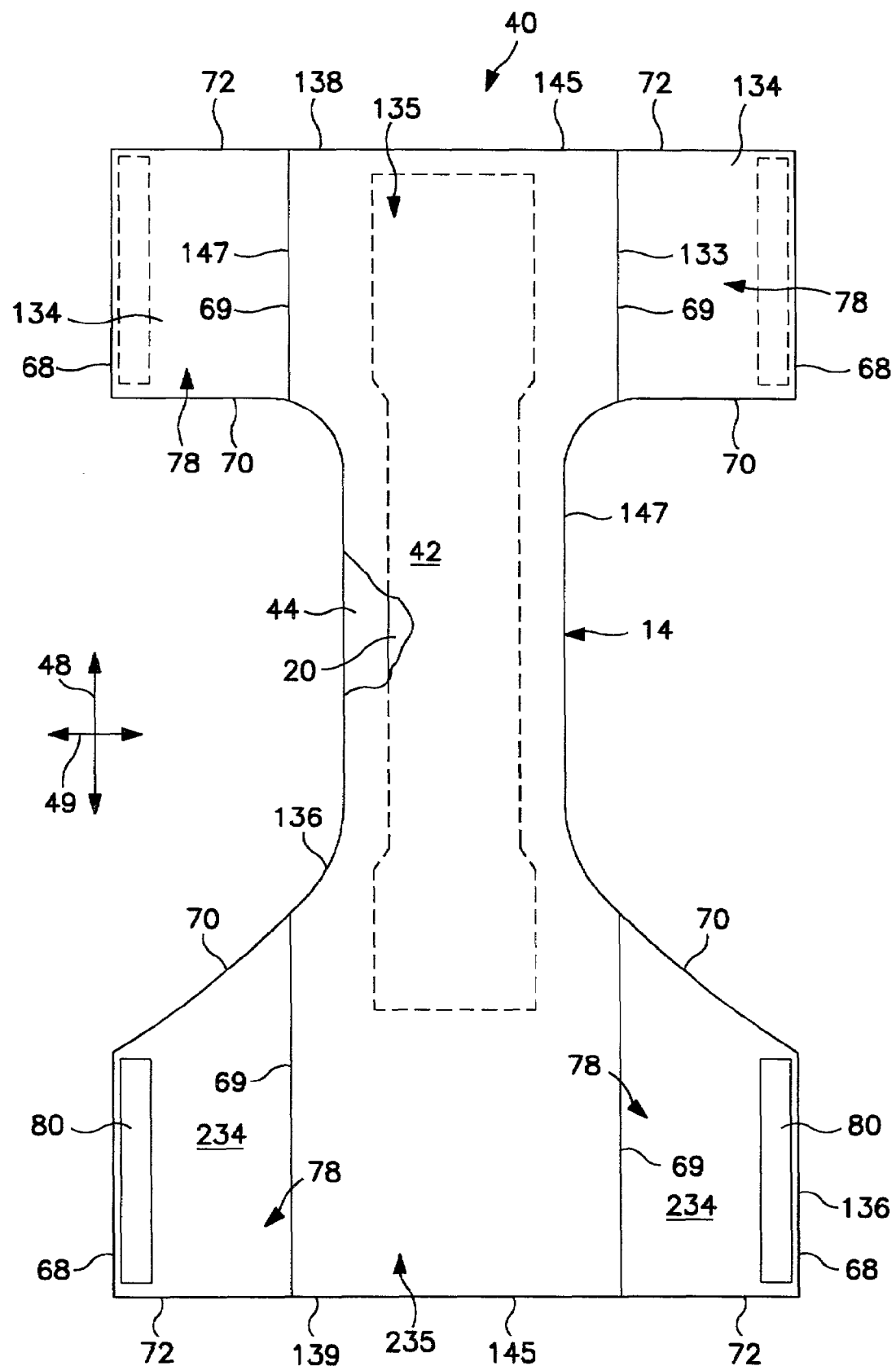
FIG. 2 is a plan view of a child's training pant in a partially disassembled, stretched flat state, showing the surface of the article that faces the wearer when the article is worn, and with portions cut away to show the underlying features including an absorbent pad.

"Longitudinal" and "transverse" have their customary meaning, as indicated by the longitudinal and transverse axes depicted in FIG. 2. The longitudinal axis lies in the plane of the article and is generally parallel to a vertical plane that bisects a standing wearer into left and right body halves when the article is worn. The transverse axis lies in the plane of the article generally perpendicular to the longitudinal axis. The article as illustrated is longer in the longitudinal direction than in the transverse direction.

"Meltblown fibers" means fibers formed by extruding a molten thermoplastic material through a plurality of fine, usually circular, die capillaries as molten threads or filaments into converging high velocity heated gas (e.g., air) streams which attenuate the filaments of molten thermoplastic material to reduce their diameter, which may be to microfiber diameter. Thereafter, the meltblown fibers are carried by the high velocity gas stream and are deposited on a collecting surface to form a web of randomly dispersed meltblown fibers. Such a process is disclosed for example, in U.S. Pat. No. 3,849,241 to Butin et al. Meltblown fibers are microfibers which may be continuous or discontinuous, are generally smaller than about 0.6 denier, and are generally self-bonding when deposited onto a collecting surface. Meltblown fibers used in the present invention are preferably substantially continuous in length.

"Online" refers to an integrated, continuous process that is an integral part of the consumer absorbent product production process, typically starting from raw materials and ending with the absorbent product, typically in a packaged form.

"Polymers" include, but are not limited to, homopolymers, copolymers, such as for example, block, graft, random and alternating copolymers, terpolymers, etc. and blends and modifications thereof. Furthermore, unless otherwise specifically limited, the term "polymer" shall include all possible geometrical configurations of the material. These configurations include, but are not limited to isotactic, syndiotactic and atactic symmetries.

"Superabsorbent" or "superabsorbent material" refers to a water-swellable, water-insoluble organic or inorganic material capable, under the most favorable conditions, of absorbing at least about 15 times its weight and, more desirably, at least about 30 times its weight in an aqueous solution containing 0.9 weight percent sodium chloride. The superabsorbent materials can be natural, synthetic and modified natural polymers and materials. In addition, the superabsorbent materials can be inorganic materials, such as silica gels, or organic compounds such as cross-linked polymers.

"Surface" includes any layer, film, woven, nonwoven, laminate, composite, or the like, whether pervious or impervious to air, gas, and/or liquids.

These terms may be defined with additional language in the remaining portions of the specification.

DETAILED DESCRIPTION OF THE PRESENTLY PREFERRED EMBODIMENTS

The present invention is directed to a thin, flexible, high capacity absorbent pad. The absorbent pad can be produced with an online drum former that can be integrated with the absorbent product producing process. The absorbent pad of the present invention can suitably be incorporated into absorbent articles. The term "absorbent article" includes without limitation diapers, training pants, swim wear, absorbent underpants, baby wipes, incontinence products, feminine hygiene products and medical absorbent products (for example, absorbent medical garments, underpads, bandages, drapes, and medical wipes). As used herein, the term "incontinence products" includes absorbent underwear for children, absorbent garments for children or young adults with special needs such as autistic children or others with bladder/bowel control problems as a result of physical disabilities, as well as absorbent garments for incontinent older adults.

Figure 1:
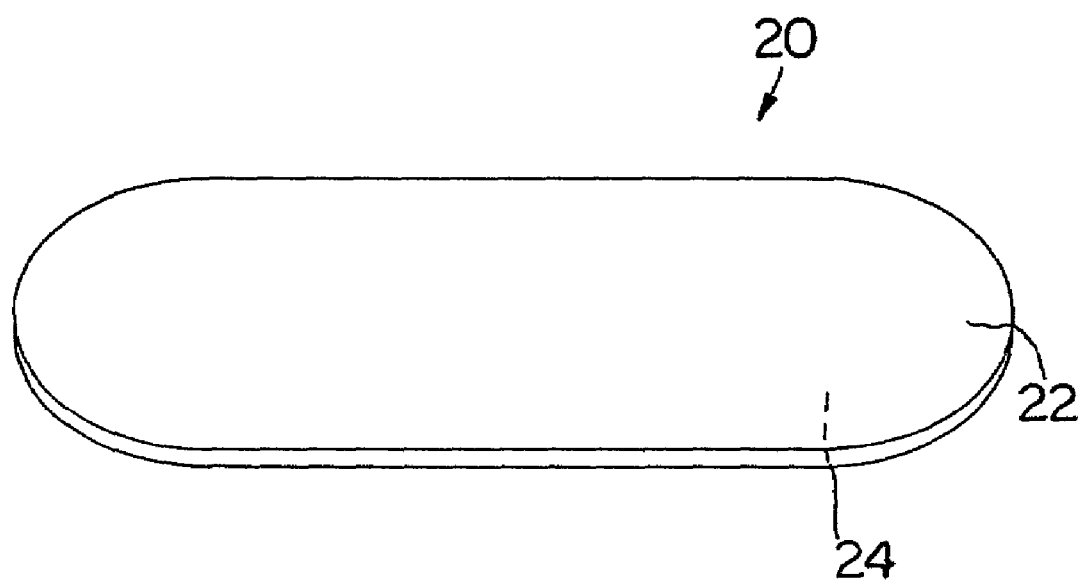
FIG. 1 is a front perspective view of an absorbent pad.

Referring to FIG. 1, an absorbent pad 20 of the present invention is illustrated. The absorbent pad 20 includes a top surface 22 which is configured to face and/or contact a wearer, and a bottom surface 24 opposite the top surface 22 which is configured to face away from a wearer. The size and shape of the absorbent pad 20 can be configured to fit within virtually any absorbent article. Examples of suitable shapes include oval, rectangular, and hourglass-shaped.

The absorbent pad 20 is generally compressible, conformable, non-irritating to a wearer's skin, and capable of absorbing and retaining liquids and certain body wastes. The absorbent pad 20 contains high levels of superabsorbent polymer (SAP), homogeneously mixed with cellulose fluff pulp. In one embodiment, the mixture of SAP and cellulose fluff pulp is homogeneous throughout the entire absorbent pad 20. In another embodiment, the SAP forms a gradient within the absorbent pad 20. For example, more SAP may be present at one end of the absorbent pad 20 than at an opposite end of the absorbent pad 20. Alternatively, more SAP may be present along a top surface of the absorbent pad 20 than along a bottom surface of the absorbent pad 20. As yet another alternative, more SAP may be present along the bottom surface of the absorbent pad 20 than along the top surface of the absorbent pad 20. Due to the gradient, the concentration of SAP can vary throughout the absorbent pad 20 by about 0.01 to about 0.40 grams per cubic centimeter, or by about 0.05 to about 0.35 grams per cubic centimeter, or by about 0.15 to about 0.25 grams per cubic centimeter.

Superabsorbent levels can range between 30 and 85 wt %, suitably between 40 and 80 wt %, more suitably between 50 and 75 wt % based on total weight of the absorbent pad. Consequently, levels of fluff pulp can range between 15 and 70 wt %, suitably between 20 and 60 wt %, more suitably between 25 and 50 wt % based on total weight of the absorbent pad. High levels of SAP and high density compaction of the formed pads 20 are required to produce this thin, high capacity invention.

The absorbent pad 20 is compacted to a thickness of between about 0.5 and 3.0 millimeters (mm), suitably between about 0.6 and 2.5 mm, more suitably between about 0.7 and 2.0 mm. As a result, the density of the absorbent pad 20 is at least 0.28 grams per cubic centimeter (g/cc). Suitably, the density of the absorbent pad is at least 0.30 g/cc. More suitably, the density of the absorbent pad is at least 0.32 g/cc.

The superabsorbent material used in the absorbent pad 20 of the present invention must be able to absorb a liquid under an applied load. As used herein, the Absorbency Under Load (AUL) value of a particular superabsorbent material refers to the amount, in grams, of an aqueous solution of sodium chloride (0.9 weight percent sodium chloride) which 1 gram of superabsorbent material can absorb in 60 minutes while under a given restraining load.

The absorbent pad 20 of the invention suitably has an absorbent saturation capacity between about 14 and 40 grams 0.9 w/v % saline solution per gram of absorbent pad, alternatively at least 16 grams/gram, or as another alternative at least 18 grams/gram. The method by which the absorbent saturation capacity is determined is set forth in detail below. Furthermore, the absorbent pad 20 of the invention suitably contains a high gel strength superabsorbent.

The cellulose fluff pulp suitably includes wood pulp fluff. The wood pulp fluff can be exchanged with synthetic, polymeric, meltblown fibers or with a combination of meltblown fibers and natural fibers. Synthetic fibers are not required in the absorbent pad 20 of the invention, but may be included in minimal amounts. One preferred type of fluff is identified with the trade designation CR1654, available from U.S. Alliance, Childersburg, Ala., U.S.A., and is a bleached, highly absorbent sulfate wood pulp containing primarily soft wood fibers. A special densification pulp, identified with the trade designation ND-416, available from Weyerhaeuser of Federal Way, Wash., U.S.A., may offer some edge compression benefits. As mentioned, the cellulose fluff pulp is homogeneously mixed with the SAP. The homogeneously mixed fluff and superabsorbent particles can be selectively placed into desired zones of higher concentration to better contain and absorb body exudates. For example, the mass of the homogeneously mixed fluff and superabsorbent particles can be controllably positioned such that more basis weight is present in a front portion of the pad than in a back portion of the pad.

Suitable superabsorbent materials can be selected from natural, synthetic, and modified natural polymers and materials. The superabsorbent materials can be inorganic materials, such as silica gels, or organic compounds, including natural materials such as agar, pectin, guar gum, and the like, as well as synthetic materials, such as synthetic hydrogel polymers. Such hydrogel polymers include, for example, alkali metal salts of polyacrylic acids; polyacrylamides; polyvinyl alcohol; ethylene maleic anhydride copolymers; polyvinyl ethers; hydroxypropylcellulose; polyvinyl morpholinone; polymers and copolymers of vinyl sulfonic acid, polyacrylates, polyacrylamides, polyvinyl pyridine; and the like. Other suitable polymers include hydrolyzed acrylonitrile grafted starch, acrylic acid grafted starch, and isobutylene maleic anhydride copolymers and mixtures thereof. The hydrogel polymers are preferably lightly crosslinked to render the material substantially water-insoluble. Crosslinking may, for example, be by irradiation or by covalent, ionic, Van der Waals, or hydrogen bonding. The superabsorbent materials may be in any form suitable for use in absorbent structures, including, particles, fibers, flakes, spheres, and the like. In one embodiment of the present invention, the superabsorbent material includes particles of a hydrocolloid, preferably an ionic hydrocolloid.

Typically, a superabsorbent material is capable of absorbing at least about 15 times its weight in water, and desirably is capable of absorbing more than about 25 times its weight in water. Suitable superabsorbent materials are available from various commercial vendors, such as Dow Chemical Company located in Midland, Mich., U.S.A., and Stockhausen GmbH & Co. KG, D-47805 Krefeld, Federal Republic of Germany. One particular SAP useful in this invention is FAVOR® SXM 9543, available from Stockhausen GmbH & Co. This SAP provides both good processability and functional performance in the absorbent pad 20 of the invention. Other suitable types of superabsorbent materials are described in U.S. Pat. No. 5,601,542 issued Feb. 11, 1997, to Melius et al.; U.S. patent application Ser. No. 09/475,829 filed in December 1999 and assigned to Kimberly-Clark Corporation; and U.S. patent application Ser. No. 09/475,830 filed in December 1999 and assigned to Kimberly-Clark Corporation; each of which is hereby incorporated by reference.

Superabsorbent materials suitable for use in the present invention are polyacrylate materials obtained from Stockhausen under the designations FAVOR® SXM 77 and FAVORS SXM 880, as well as polyacrylate materials obtained from Dow Chemical, USA under the designation of DryTech 2035. Gel strength and permeability data for these superabsorbent materials are listed in Table 1. The gel strength of the superabsorbent is above 0.65, suitably above 0.75, more suitably above 0.85.

TABLE 1

Superabsorbent Gel Strength and Permeability

| Superabsorbent | Gel Strength | Permeability ($e^{-9}cm^2$) |
|---|---|---|
| FAVOR ® SXM 9543 | 0.9 | 300 |
| FAVOR ® SXM 880 | 0.7 | 80 |
| FAVOR ® SXM 77 | 0.6 | 15 |
| DryTech 2035 | 0.4 | 40 |

The superabsorbent material can be in the form of particles which, in the unswollen state, have maximum cross-sectional diameters within the range of from about 50 microns to about 1,000 microns, preferably within the range of from about 100 microns to about 800 microns, as determined by sieve analysis according to American Society for Testing Materials (ASTM) Test Method D-1921. It is understood that the particles of superabsorbent material, falling within the ranges described above, may include solid particles, porous particles, or may be agglomerated particles including many smaller particles agglomerated into particles within the described size ranges.

The absorbent pad 20 may also contain other components, such as man-made fibers or filler particles, such as clays. The absorbent pad 20 may also contain any of a variety of chemical additives or treatments, fillers or other additives, such as clay, zeolites and other odor-absorbing material, for example activated carbon carrier particles or active particles such as zeolites and activated carbon. The absorbent pad 20 may also include binder fibers, such as bicomponent fibers, as up to about 4% of the weight of the absorbent pad. The absorbent pad 20 may or may not be wrapped or encompassed by a suitable tissue wrap that maintains the integrity and/or shape of the absorbent pad.

The densified pads 20 exhibit good edge compression properties for user comfort and acceptance. The method by which edge compression can be measured is set forth in detail below. Absorbent performance of the thin, high capacity absorbent pads 20 is comparable to conventional, low density absorbent pads.

FIG. 2 shows a child's training pant in a partially disassembled, stretched flat state with the absorbent pad of the invention incorporated therein, showing a surface of the training pant that faces the wearer when the garment is worn. An absorbent chassis 14 defines a pair of transversely opposed side edges 136 and a pair of longitudinally opposed waist edges, which are designated front waist edge 138 and back waist edge 139. When the training pant is in a fastened position (not shown), the absorbent chassis also defines a waist opening along the front waist edge 138 and the back waist edge 139 and two leg openings along the transversely opposed side edges 136. The chassis 14 also includes a somewhat rectangular composite structure 133, a pair of transversely opposed front side panels 134, and a pair of transversely opposed back side panels 234. The composite structure 133 and side panels 134 and 234 may be integrally formed, or may include two or more separate elements, as shown in FIG. 2.

The illustrated composite structure 133 includes an outer cover 44, a body side liner 42 which is connected to the outer cover in a superposed relation, and the absorbent pad 20 of the invention which is located between the outer cover 44 and the body side liner 42. The rectangular composite structure 133 has opposite linear end edges 145 that form portions of the front and back waist edges 138 and 139, and opposite linear, or curvilinear, side edges 147 that form portions of the side edges 136 of the absorbent chassis 14. For reference, arrows 48 and 49 depicting the orientation of the longitudinal axis and the transverse axis, respectively, of the training pant 20 are illustrated in FIG. 2.

The liquid permeable body side liner 42 is illustrated as overlying the outer cover 44 and the absorbent pad 20 (FIG. 2), and may but need not have the same dimensions as the outer cover 44. The body side liner 42 is desirably compliant, soft feeling, and non-irritating to the child's skin. Further, the body side liner 42 can be less hydrophilic than the absorbent pad 20, to present a relatively dry surface to the wearer and permit liquid to readily penetrate through its thickness. The absorbent pad 20 (FIG. 2) is positioned between the outer cover 44 and the body side liner 42, which components can be joined together by any suitable means, such as adhesives, as is well known in the art.

The absorbent chassis 14 can also incorporate other materials that are designed primarily to receive, temporarily store, and/or transport liquid along the mutually facing surface with the absorbent pad 20, thereby maximizing the absorbent capacity of the absorbent assembly. One suitable material is referred to as a surge layer (not shown) and can be, for example, a material having a basis weight of about 50 grams per square meter, and including a through-air-bonded-carded web of a homogenous blend of 60 percent 3 denier bicomponent fiber including a polyester core/polyethylene sheath, commercially available from KoSa Corporation, and 40 percent 6 denier polyester fiber, commercially available from KoSa Corporation, in Salisbury, N.C., U.S.A. Other surge compositions are possible, and selected materials are described herein.

The outer cover 44 desirably includes a material that is substantially liquid impermeable, and can be elastic, stretchable or nonstretchable. The outer cover 44 can be a single layer of liquid impermeable material, but desirably includes a multi-layered laminate structure in which at least one of the layers is liquid impermeable. For instance, the outer cover 44 can include a liquid permeable outer layer and a liquid impermeable inner layer that are suitably joined together by a laminate adhesive (not shown). Suitable laminate adhesives, which can be applied continuously or intermittently as beads, a spray, parallel swirls, or the like, can be obtained from Findley Adhesives, Inc., of Wauwatosa, Wisc., U.S.A., or from National Starch and Chemical Company, Bridgewater, N.J., U.S.A. The liquid permeable outer layer can be any suitable material and desirably one that provides a generally cloth-like texture. One example of such a material is a 20 gsm (grams per square meter) spunbond polypropylene nonwoven web. The outer layer may also be made of those materials of which liquid permeable bodyside liner 42 is made. While it is not a necessity for the outer layer to be liquid permeable, it is desired that it provides a relatively cloth-like texture to the wearer.

The inner layer of the outer cover 44 can be both liquid and vapor impermeable, or can be liquid impermeable and vapor permeable. The inner layer is desirably manufactured from a thin plastic film, although other flexible liquid impermeable materials may also be used. The inner layer, or the liquid impermeable outer cover 44 when a single layer, prevents waste material from wetting articles, such as bedsheets and clothing, as well as the wearer and caregiver. A suitable liquid impermeable film for use as a liquid impermeable inner layer, or a single layer liquid impermeable outer cover 44, is a 0.02 millimeter polyethylene film commercially available from Huntsman Packaging of Newport News, Va., U.S.A. If the outer cover 44 is a single layer of material, it can be embossed and/or matte finished to provide a more cloth-like appearance. As earlier mentioned, the liquid impermeable material can permit vapors to escape from the interior of the disposable absorbent article, while still preventing liquids from passing through the outer cover 44. A suitable "breathable" material is composed of a microporous polymer film or a nonwoven fabric that has been coated or otherwise treated to impart a desired level of liquid impermeability. A suitable microporous film is a PMP-1 film material commercially available from Mitsui Toatsu Chemicals, Inc., Tokyo, Japan, or an XKO-8044 polyolefin film commercially available from 3M Company, Minneapolis, Minn. Other similar materials with varying degrees of liquid permeability are spunbond meltblown webs, spunbond/meltblown/spunbond hydrophobic, uniformly formed spunbond, or bi-component webs. A balance of barrier and permeability can be adjusted with fiber size and basis weight.

The bodyside liner 42 can be manufactured from a wide selection of web materials, such as synthetic fibers (for example, polyester or polypropylene fibers), natural fibers (for example, wood or cotton fibers), a combination of natural and synthetic fibers, porous foams, reticulated foams, apertured plastic films, or the like. Various woven and nonwoven fabrics can be used for the bodyside liner 42. For example, the bodyside liner can be composed of a meltblown or spunbonded web of polyolefin fibers. The bodyside liner can also be, a bonded-carded web composed of natural and/or synthetic fibers. The bodyside liner can be composed of a substantially hydrophobic material, and the hydrophobic material can, optionally, be treated with a surfactant or otherwise processed to impart a desired level of wettability and hydrophilicity. For example, the material can be surface treated with about 0.28 weight percent of a surfactant commercially available from the Rohm and Haas Co. under the trade designation Triton X-102. Other suitable surfactants are commercially available from Uniqema Inc., a division of ICI of New Castle, Del., under the trade designation Ahcovel, and from Cognis Corporation of Ambler, Pa., produced in Cincinnati, Ohio, and sold under the trade designation Glucopon 220. The surfactant can be applied by any conventional means, such as spraying, printing, brush coating or the like. The surfactant can be applied to the entire bodyside liner 42 or can be selectively applied to particular sections of the bodyside liner, such as the medial section along the longitudinal centerline.

A suitable liquid permeable bodyside liner 42 is a nonwoven bicomponent web having a basis weight of about 27 gsm. The nonwoven bicomponent can be a spunbond bicomponent web, or a bonded carded bicomponent web. Suitable bicomponent staple fibers include a polyethylene/polypropylene bicomponent fiber available from CHISSO Corporation, Osaka, Japan. In this particular bicomponent fiber, the polypropylene forms the core and the polyethylene forms the sheath of the fiber. Other fiber orientations are possible, such as multi-lobe, side-by-side, islands in the sea, or the like. While the outer cover 44 and bodyside liner 42 can include elastomeric materials, it can be desirable in some embodiments for the composite structure to be generally inelastic, where the outer cover, the bodyside liner and the absorbent assembly include materials that are generally not elastomeric.

As noted previously, the illustrated training pant 20 can have front and back side panels 134 and 234 disposed on each side of the absorbent chassis 14 (FIG. 2). These transversely opposed front side panels 134 and transversely opposed back side panels 234 can be permanently bonded to the composite structure 133 of the absorbent chassis 14 and can be releasably attached to one another by a fastening system 80. More particularly, as shown best in FIG. 2, the front side panels 134 can be permanently bonded to and extend transversely beyond the linear side edges 147 of the composite structure 133 along attachment lines 69, and the back side panels 234 can be permanently bonded to and extend transversely beyond the linear side edges of the composite structure along attachment lines 69. The side panels 134 and 234 may be attached using attachment means known to those skilled in the art such as adhesive, thermal or ultrasonic bonding. The side panels 134 and 234 can also be formed as a portion of a component of the composite structure 133, such as the outer cover 44 or the body side liner 42.

Each of the side panels 134 and 234 can include one or more individual, distinct pieces of material. In particular embodiments, for example, each side panel 134 and 234 can include first and second side panel portions that are joined at a seam, with at least one of the portions including an elastomeric material (not shown). Still alternatively, each individual side panel 134 and 234 can include a single piece of material which is folded over upon itself along an intermediate fold line (not shown).

The side panels 134 and 234 desirably include an elastic material capable of stretching in a direction generally parallel to the transverse axis 49 of the training pant 20. In particular embodiments, the front and back side panels 134 and 234 may each include an interior portion 78 disposed between a distal edge 68 and a respective front or back center panel 135 or 235. In the illustrated embodiment in FIG. 2, the interior portions 78 are disposed between the distal edges 68 and the side edges 147 of the rectangular composite structure 133. The elastic material of the side panels 134 and 234 can be disposed in the interior portions 78 to render the side panels elastomeric in a direction generally parallel to the transverse axis 49. Most desirably, each side panel 134 and 234 is elastomeric from a waist end edge 72 to a leg end edge 70. More specifically, individual samples of side panel material, taken between the waist end edge 72 and the leg end edge 70 parallel to the transverse axis 49 and having a length from the attachment line 69 to the distal edge 68 and a width of about 2 centimeters, are all elastomeric.

Suitable elastic materials, as well as one described process of incorporating elastic side panels into a training pant, are described in the following U.S. Pat. Nos.: 4,940,464 issued Jul. 10, 1990 to Van Gompel et al.; 5,224,405 issued Jul. 6, 1993 to Pohjola; 5,104,116 issued Apr. 14, 1992 to Pohjola; and 5,046,272 issued Sep. 10, 1991 to Vogt et al.; all of which are incorporated herein by reference. In particular embodiments, the elastic material includes a stretch-thermal laminate (STL), a neck-bonded laminated (NBL), a reversibly necked laminate, or a stretch-bonded laminate (SBL) material. Methods of making such materials are well known to those skilled in the art and described in U.S. Pat. No. 4,663,220 issued May 5, 1987 to Wisneski et al.; U.S. Pat. No. 5,226,992 issued Jul. 13, 1993 to Morman; and European Patent Application No. EP 0 217 032 published on Apr. 8, 1987 in the names of Taylor et al.; all of which are incorporated herein by reference. Alternatively, the side panel material may include other woven or nonwoven materials, such as those described above as being suitable for the outer cover 44 or body side liner 42, or stretchable but inelastic materials.

As described herein, the various components of the training pant 20 can be integrally assembled together employing various types of suitable attachment means, such as adhesive, sonic and thermal bonds or combinations thereof. The resulting product is an absorbent garment 20 including a thin, flexible, high capacity absorbent pad 20. The pant-like absorbent garment 20 can be sized and tailored for a wide variety of uses including, for example, diapers, training pants, swim wear, incontinence garments, and the like.

Figure 3:
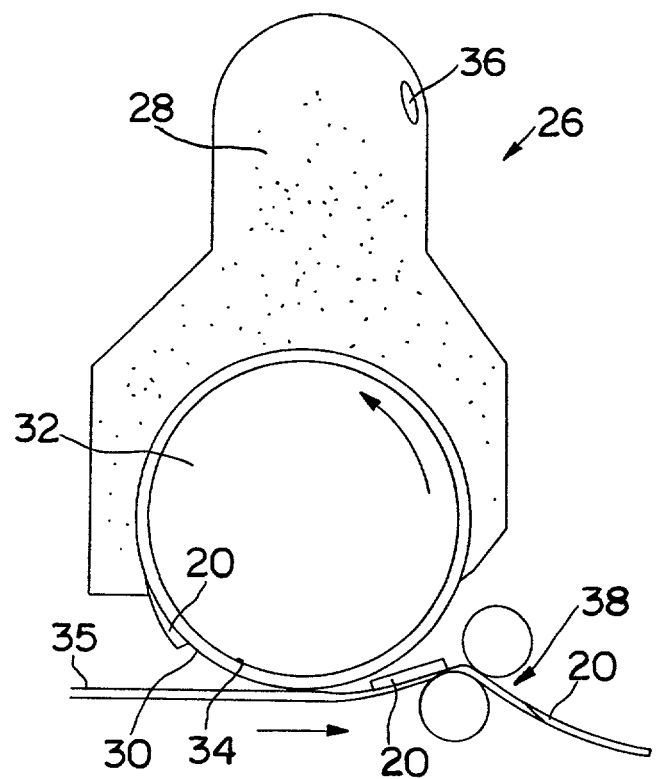
FIG. 3 is a plan view of apparatus used to make an absorbent pad.

The absorbent pad 20 of the invention can be produced using a conventional online absorbent drum former 26, as shown in FIG. 3. More specifically, the SAP and the fluff pulp can be homogeneously mixed in a forming chamber 28 of the drum former 26. As mentioned, man-made fibers or carrier particles can also be mixed with the SAP and the fluff pulp. To minimize SAP loss during forming, a porous fabric 30, such as a woven polyester fabric with approximately 300 micron pores, can be wrapped around a forming drum 32 of the drum former 26 to cover a forming screen 34 on the forming drum 32. Alternatively, fine pore, or micro-perforated, forming screens can be used in place of conventional forming screens 34. As another alternative, a light layer of fluff pulp-rich composite can be directed to the forming screens 34 prior to having the high-SAP composition reach the forming screens 34 within the forming chamber 28. In any case the effective openings of the screen surface are less than 300 microns. The permeability of the forming surface must be high enough to form a uniform pad and the forming surface must be durable. This combination of properties dictates a pore size between 75 and 300 microns. The forming screens 34, whether conventional or fine pore, can be either flat screens or shaped pad zoned absorbent screens.

By using an online drum former 26, as opposed to producing the absorbent pads 20 offline, additional mass of the homogeneously mixed superabsorbent material and pulp fluff can be directed into at least one area of the absorbent pad where extra absorbent material would be most useful.

Figure 4:
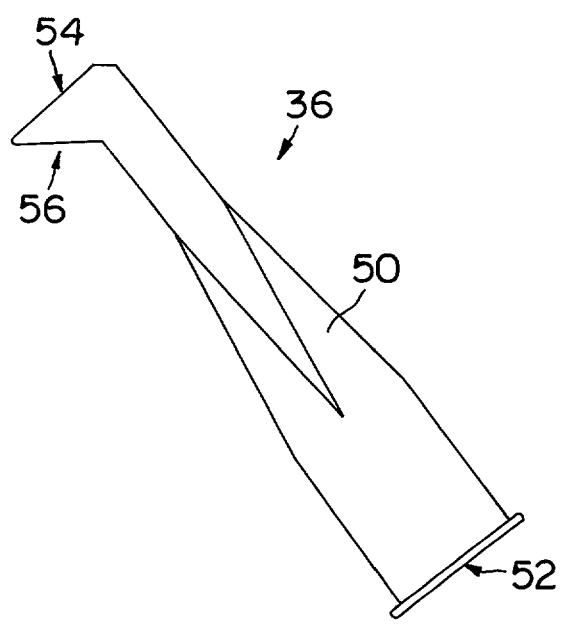
FIG. 4 is a plan view of a mixing nozzle used to homogeneously mix superabsorbent material and pulp fluff.

A special SAP nozzle 36, shown in FIG. 4, can be placed in a top front position on the forming chamber 28. The nozzle 36 includes a flattened and expanded pipe 50 that forms a slot 52, and a hood 54 projecting partially over a terminal opening 56 of the nozzle 36. This nozzle 36 disperses the SAP and enables homogeneous mixing of the SAP and the fluff pulp, or can be positioned to provide a gradient of composition within the pad.

The formed pad 20 leaves the forming chamber 28 at a low density, to namely less than 0.1 g/cc, and must be densified. The pads are deposited on a conveyor or carrier tissue 35. This invention requires that the pads undergo compaction to a density of at least 0.28 g/cc, suitably at least 0.30 g/cc, more suitably at least 0.32 g/cc. The densification can be accomplished with a conventional compaction roll, or more suitably, with a heated nip 38 as shown in FIG. 3. The heated nip 38 is suitably heated to about 80 to about 150 degrees Celsius. The pads can be produced with a basis weight of between about 80 and 1000 gsm, suitably between about 100 and 800 gsm, more suitably between about 120 and 750 gsm. Once the pads are densified, the pads have a thickness of between about 0.4 and 3.0 mm, suitably between about 0.5 and 2.5 mm, more suitably between about 0.6 and 2.0 mm.

During the forming process, the mixture of SAP and pulp fluff can be humidified to improve densification of the resulting absorbent pad 20 and to possibly provide lower edge compression or stiffness values. The use of heat and humidity in the absorbent composite densification process is taught, for example, in U.S. Pat. No. 6,214,274 issued Apr. 10, 2001, to Melius et al., which is herein incorporated by reference. Furthermore, a pattern can be embossed onto the absorbent pad 20 which may also reduce stiffness.

EXAMPLE 1

In this example, eight different sample absorbent pads were produced using the on-line forming drum of a PULL-UPS® Disposable Training Pants production machine. The pads possessed differing compositions and densities, and were tested to determine their absorption time and intake time. The various types of SAP used included a SAP having high gel strength available under the trade designation FAVOR® SXM 9543, available from Stockhausen GmbH & Co. KG, D-47805 of Krefeld, Federal Republic of Germany; and a polyacrylate material available from Stockhausen under the trade designation FAVOR® SXM 880. The various types of pulp fluff used included a bleached, highly absorbent sulfate wood pulp available under the trade designation CR1654, available from U.S. Alliance, Childersburg, Ala., U.S.A.; a bleached southern softwood pulp available under the trade designation NB-416, available from Weyerhaeuser Corporation of Federal Way, Wash., U.S.A.; a southern softwood pulp that has been cold caustic treated and is available under the trade designation AL9401, available from Rayonier Incorporated, Stamford, Conn.; and a special densification pulp available under the trade designation ND-416, available from Weyerhaeuser Corporation. Table 2 shows the composition and density of each of the samples tested.

TABLE 2

Sample Compositions and Densities

| Sample | Composition | Density (g/cc) |
|---|---|---|
| Code 1 | 50% FAVOR ® SXM 9543, 50% CR1654 | 0.32 |
| Code 2 | 50% FAVOR ® SXM 9543, 50% NB-416 | 0.32 |
| Code 3 | 50% FAVOR ® SXM 9543, 50% AL9401/NB-416 (~1:1 blend) | 0.33 |

TABLE 2-continued

Sample Compositions and Densities

| Sample | Composition | Density (g/cc) |
|---|---|---|
| Code 4 | 40% FAVOR ® SXM 9543, 60% AL9401/NB-416 (~1:1 blend) | 0.28 |
| Code 5 | 50% FAVOR ® SXM 9543, 50% ND-416 | 0.34 |
| Code 6 | 50% FAVOR ® SXM 880, 50% CR1654 | 0.35 |
| Code 7 | 44% FAVOR ® SXM 880, 56% CR1654 | 0.22 |
| Code 8 | 50% FAVOR ® SXM 880, 50% CR1654 | 0.21 |

The samples were prepared by cutting a 6-inch by 4.5-inch piece of each sample from the formed pad. The weight and bulk of each of the samples was then recorded.

Four different types of surge layers were tested with a sample of each absorbent pad. These surge layers were through-air bonded carded webs including bicomponent fibers and polyester fibers. A first surge material contained 60 wt % 2.8 denier T-256 bicomponent fibers produced by KoSa and 40 wt % T-295 6 denier polyester fibers produced by KoSa. A second surge material contained 60 wt % of a 2.0 denier T-256 type bicomponent fiber and 40 wt % of a 3.0 denier KoSa polyester fiber. All surges were 62 mm wide. The four different types of surge layers included a 55 grams per square meter (gsm) surge made of the first surge material, an 85 gsm surge made of the second surge material, a 100 gsm surge made of the first surge material and a 100 gsm surge made of the second surge material.

A sample of each of Codes 1-8 was combined with a 5-inch length of each of the four surge layers, each surge layer tested separately, a 10-inch length of liner material, and a 10-inch length of poly film. The liner material used was 0.6 osy spunbond treated with 0.3% Ahcovel, produced by Kimberly-Clark Corporation. The poly film used was 0.75 mil polyethylene film, available from Edison Plastics. An entire surface of each piece of poly film was lightly sprayed with a hot melt adhesive, namely Ato Findley 2525A, available from Ato Findley, and the sample of absorbent material was placed in the center of the poly film on the sprayed surface. The surge layer was then attached to the center of the absorbent with another light spray of the adhesive. The liner was then placed on top of the surge layer, thereby forming a seal with the poly film around the absorbent.

The insult point was then marked in the center of each sample, approximately 3 inches from each end. The dry weight of each sample was then measured and recorded.

Figure 5:
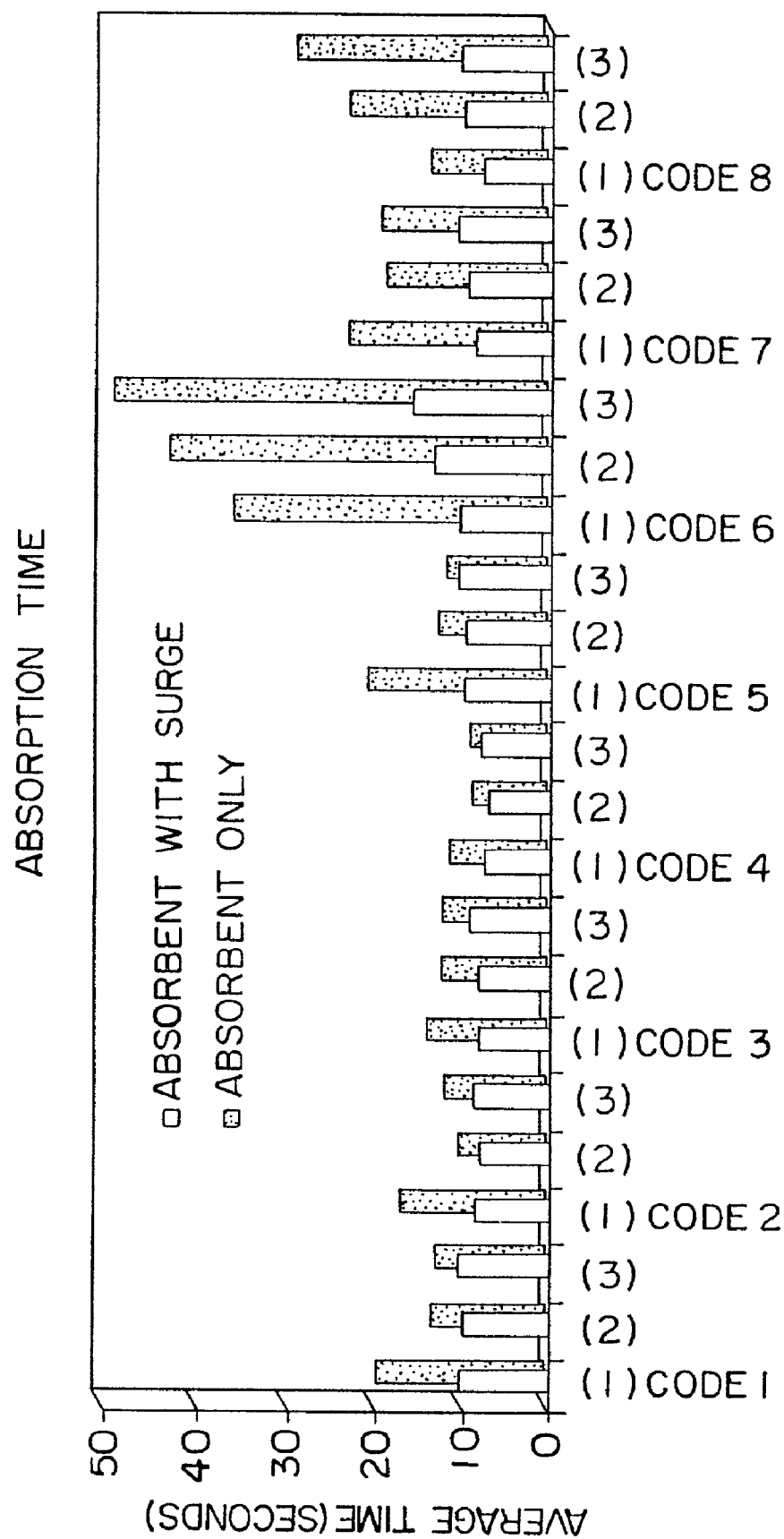
FIG. 5 is a chart showing the absorption time of various absorbent pads.

To test the absorption time of each sample, each sample was tested without a surge layer, and also with a 55 gsm surge layer. The test sample was placed between parallel, rigid plexiglass plates. The top plate had a centrally located cylindrical opening, one inch in diameter, that was placed above the insult point and was used to direct liquid into the product. The bottom plate had a 4.5-inch by 4.5-inch centrally located raised platform. The top plate exerted a 385 gram load on the 20.25 square inches of the absorbent positioned on the platform of the bottom plate. Approximately 35 ml of 0.9 w/v % saline solution was poured onto the insult point of each sample being tested and was considered to be absorbed when all of the liquid was visually determined to have penetrated the surface of the absorbent, at which time the intake time was recorded. Again, a 35 ml insult was poured onto the insult point of each sample and the absorption time of the second insult was then recorded. Finally, a third 35 ml insult was poured onto the insult point of each sample and the absorption time of the third insult was then recorded. Time between insults was 15 to minutes. The results of this test for Codes 1-8 are shown in the chart in FIG. 5. The results in FIG. 5 indicate that at equivalent composition and density, FAVOR® SXM 9543 is shown to have overall performance superior to that of FAVOR® SXM 880 over the course of three insults, whether or not a surge layer is present. In addition, all high density codes, with the exclusion of Code 6, are equivalent or superior in performance to the control low-density codes, 7 and 8.

Figure 6:
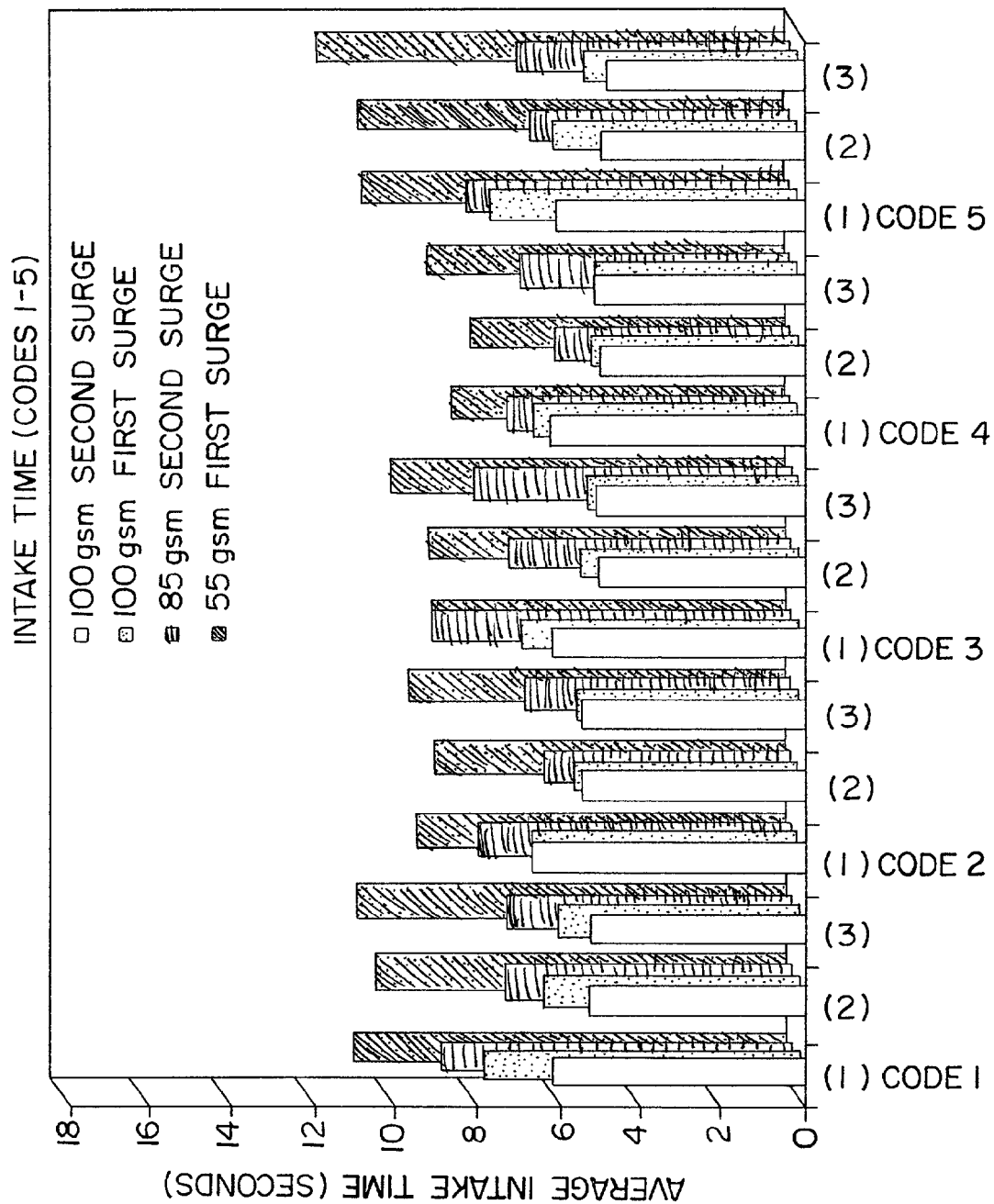
FIG. 6 is a chart showing the intake time of 5 of 8 various absorbent pads tested.
Figure 7:
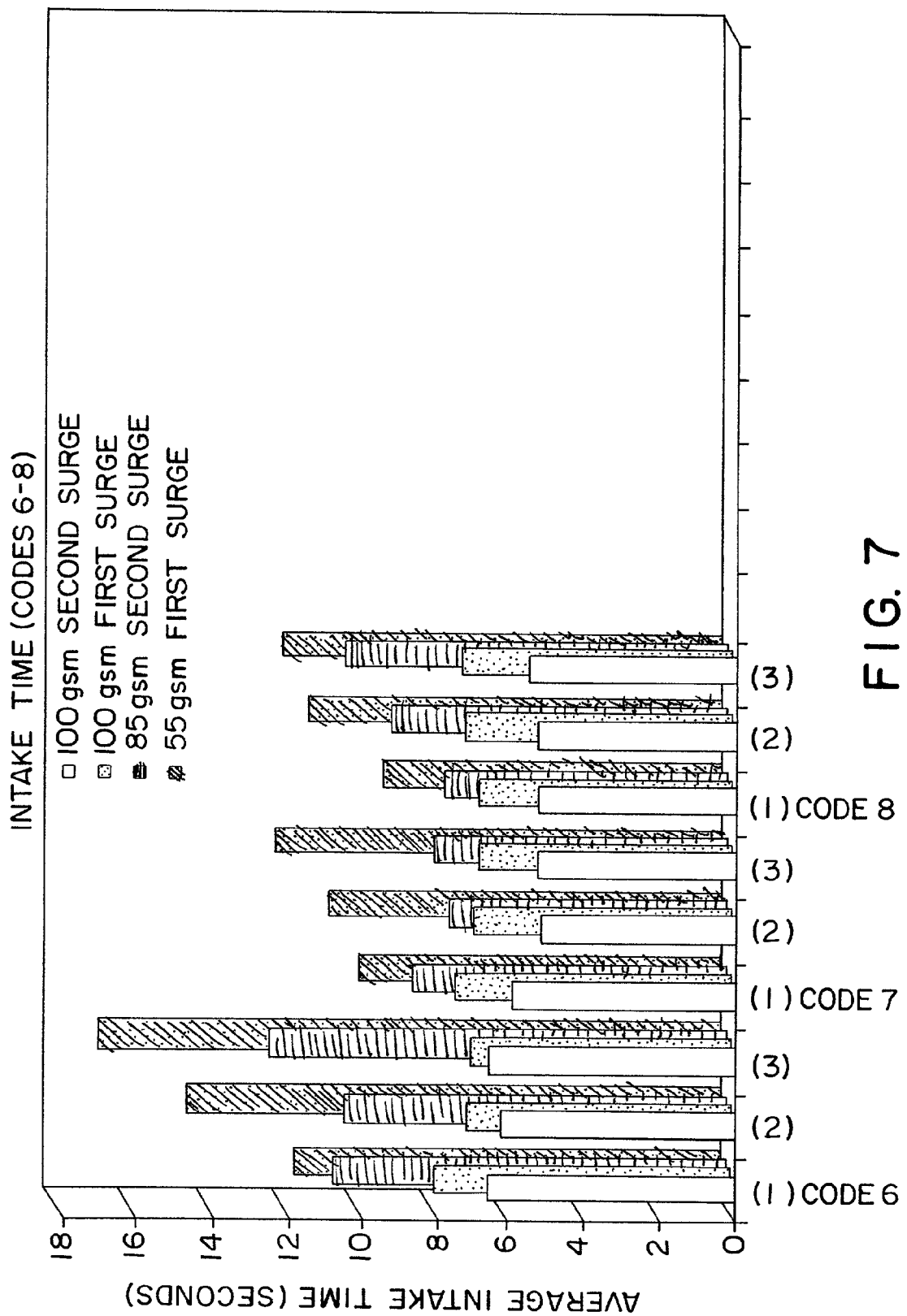
FIG. 7 is a chart showing the intake time of 3 of 8 various absorbent pads tested.

To test the intake time of each sample, each sample was tested with each of the four types of surge layers, using the procedure described immediately following, in which three 35 mL insults are applied to each sample. The results of this test for Codes 1-5 are shown in the chart in FIG. 6 and the results of this test for Codes 6-8 are shown in the chart in FIG. 7. As can be seen in FIGS. 6 and 7, the lowest consistent intake time was observed in the samples made using the 100 gsm second surge layer, described above, with the intake time of each of the samples being fairly consistent with one another. Comparing the samples using the other three surge layers, the sample having the highest percentage of SAP, namely Code 4, outperformed the other samples.

EXAMPLE 2

In this example, absorbent pads were produced using the online forming drum of a PULL-UPS® Disposable Training Pants production machine. The machine was configured so that absorbent pads could be extracted from the process line just before combining with other components in the product assembly process. This permitted evaluation of the online formed pads without having to disassemble finished product. This trial used rectangular shaped, uniform depth, forming screens with micro-perforated screen openings produced by FT&D located in Helen, Ga. The microperf screens were able to prevent SAP from passing into the interior of the forming drum, similar to a fine mesh fabric wrap. This produced consistent absorbent weights, even at SAP levels exceeding 65%. Airflow uniformity and volume were maintained in the normal operating range and resulted in good pad formation.

Adding small amounts of moisture to the absorbent was desired as a means of reducing the pressure required to achieve densities greater than 0.3 g/cc. Rather than spraying moisture onto the absorbent, drawing humidified air through the pad was selected to provide a more uniform distribution of the moisture through the thickness of the absorbent. A heating element and blower motor were used to pipe hot air to a hood installed over the vacuum conveyor between the forming drum and the pre-debulker. Filtered tap water was merged with compressed air (20 psi) and introduced into the warm air stream as a fine mist via an atomizing spray nozzle with a 0.028 inch opening. A humidity of approximately 40% RH at an air temperature of 120 degrees Celsius was achieved in the air stream. Once the best moisture conditions were achieved, absorbent pads were produced. Approximately 1% moisture determined by change in weight of pads was added to the pads via this technique. Humidification in this way permitted opening the compaction roll 5 mils while achieving the same absorbent pad caliper.

Use of heated compaction rolls also reduces the force required to densify absorbent compositions of this invention. However, the following examples, shown in Table 3, were produced without heat or added moisture to demonstrate some characteristics of the invention.

TABLE 3

Comparison of Ultra-Thin Absorbents to a Standard Absorbent

| Sample | Basis Weight (gsm) | SAP | Pulp | SAP Weight (g) | Pulp Weight (g) | Sat Cap (g) | Bulk (mm) | Density (g/cc) | Description |
|---|---|---|---|---|---|---|---|---|---|
| 1 | 715 in front; 525 in back | 44% | CR1654 | 13 | 16.5 | 580 | 4.8 in front; 2.6 in back | 0.15 in front; 0.2 in back | Large PULL-UPS ® |
| 2 | 670 | 60% | NB416 | 14.8 | 9.9 | 490 | 1.8 | 0.37 | UTA |
| 3 | 670 | 60% | NB416 | 14.8 | 9.9 | 480 | 1.8 | 0.37 | UTA with moisture |
| 4 | 510 | 60% | NB416 | 11.3 | 7.5 | 395 | 1.4 | 0.36 | Low cap UTA |
| 5 | 260 | 30% | NB416 | 2.9 | 6.7 | 150 | 0.7 | 0.37 | Low basis weight, SAP UTA |
| 6 | 200 | 50% | NB416 | 3.7 | 3.7 | 140 | 0.6 | 0.33 | Low basis weight, high SAP UTA |
| 7 | 670 | 60% | ND416 | 14.8 | 9.9 | 475 | 1.8 | 0.37 | ND416 pulp UTA |

As indicated in Table 3, the mass of Sample 1 was controllably positioned to create a greater basis weight in a front portion than in a back portion of the sample. The various types of pulp used included CR1654, NB416 and ND416, each of which is described above in Example 1. Saturated capacity ("Sat Cap") refers to the weight of the sample when saturated. The ultra-thin absorbents ("UTA") in Samples 2-7 are compared to a standard training pant in Sample 1.

All UTA codes were produced with FAVOR® SXM 9543 superabsorbent. Sample 1 was produced with Stockhausen FAVOR® SXM 880 superabsorbent and was produced with the standard large PULL-UPS® Disposable Training Pants forming screens (non-microperf). Historically, high quality, low basis weight pads are often difficult to produce with an online drum forming process but the low basis weight samples, Samples 5 and 6, were extremely supple and very uniform along the pad as well as between pads.

Superabsorbent feed rate was increased while producing Sample 2 to achieve a SAP composition of 65%. High-density versions of Samples 6 and 7 were produced by increasing the feed of SAP and pulp fibers into the forming drum, resulting in an increase in basis weight of the formed absorbent pad. The high-density version of Sample 6 was produced at a basis weight of 490 gsm with a thickness of 0.86 mm and had a density of 0.57 g/cc. The high-density version of Sample 7 had a basis weight of about 795 gsm, a thickness of 1.39 mm and a density of 0.57 g/cc.

Products containing the online ultra thin absorbent pads based on Sample 2 were produced for a large-scale consumer use test. Results of this use test showed no statistical difference in leakage performance between products with the online ultra thin absorbent compared to commercial PULL-UPS® Disposable Training Pants.

EXAMPLE 3

Figure 8:
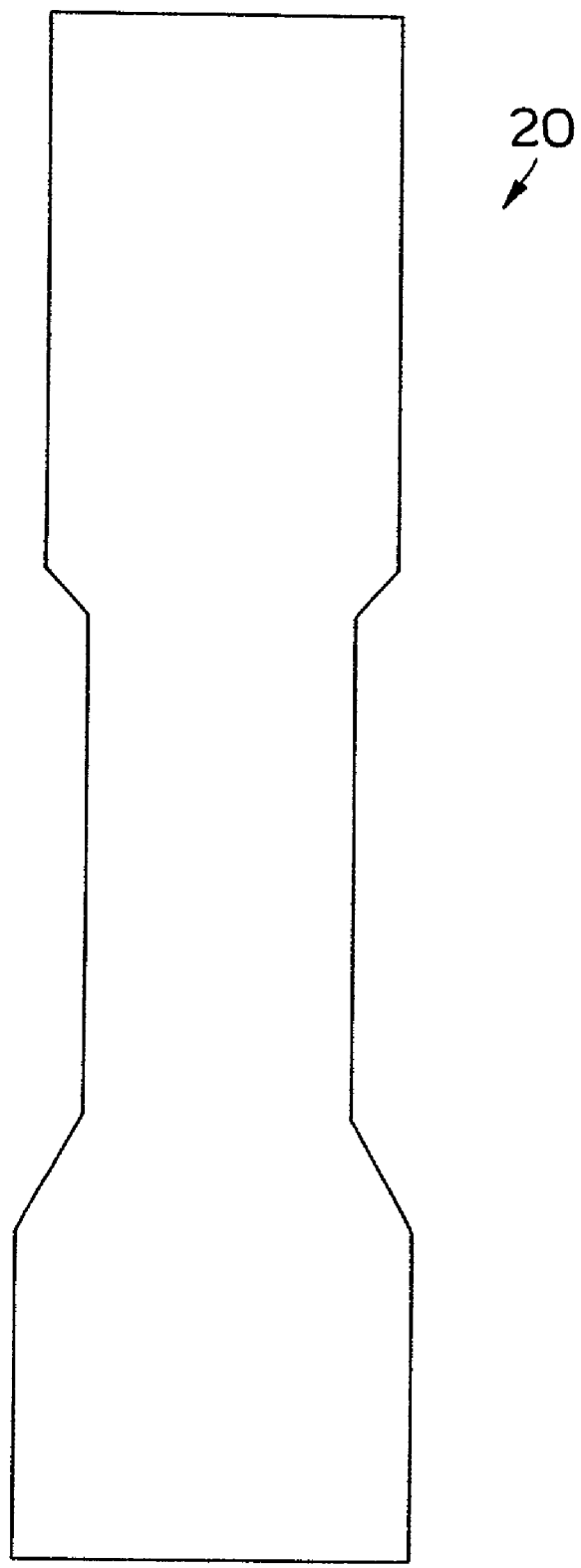
FIG. 8 is a top view of an absorbent pad having a contoured shape.

A commercial machine trial was conducted to produce online ultra thin absorbent pads and products containing the online ultra thin absorbent pads. Forming screens 34 with a contour shape, as shown in FIG. 8, were wrapped with a polyester mesh fabric. These forming screens also had a front pocket, a deep zone to allow more absorbent to be positioned in the insult zone of the product. Products were produced with contoured absorbent pads that had about 60% of the absorbent mass in the front half of the pad. Pads and products were produced at commercial line speeds, in excess of 600 feet per minute.

EXAMPLE 4

In this example, absorbent pads were again produced using the online forming drum of a PULL-UPS® Disposable Training Pants production machine. The machine was configured such that absorbent pads could be extracted from the process line just before combining with other components in the product assembly process. This permitted evaluation of the online formed pads without having to disassemble finished product. This trial used rectangular shaped, uniform depth, forming screens with micro-perforated screen openings produced by FT&D. The absorbent pads included 60% FAVOR® SXM 9543 superabsorbent and 40% Weyerhauser ND416 pulp. The bulk of the absorbents was held constant at approximately 1.9-2.0 mm. The pulp and superabsorbent feed rates were varied to produce a range in basis weight, resulting in a range of densities. The edgewise compression of these examples was evaluated and compared to the compression of the standard PULL-UPS® Disposable Training Pant absorbent composition (44% Stockhausen FAVOR® SXM 880 superabsorbent, 56% US Alliance CR1654 pulp, ~0.20 g/cc density). The result, shown in Table 4, was that the examples of the invention exhibited similar compression performance as the current absorbent composition over a range of densities considerably higher than the current structure. Even lower compression values can be achieved through low level moisture addition, heated compaction rolls, the use of embossing compaction rolls, or any combination of these techniques.

TABLE 4

Compression Comparison

| Composition | Basis Weight (gsm) | Density (g/cc) | Energy to 50% Compression (gm-cm) |
|---|---|---|---|
| 44% SAP, 56% Pulp | 846 | 0.191 | 2373.1 |
| 60% SAP, 40% Pulp | 770.5 | 0.41 | 2967.3 |
| 60% SAP, 40% Pulp | 757.6 | 0.397 | 2740.9 |
| 60% SAP, 40% Pulp | 756.9 | 0.373 | 3614.8 |

TABLE 4-continued

Compression Comparison

| Composition | Basis Weight (gsm) | Density (g/cc) | Energy to 50% Compression (gm-cm) |
|---|---|---|---|
| 60% SAP, 40% Pulp | 795.7 | 0.374 | 3068.9 |
| 60% SAP, 40% Pulp | 742.7 | 0.373 | 2726.3 |

EXAMPLE 5

An online ultra thin absorbent pad was produced at 50/50 ratio of FAVOR® SXM 9543 superabsorbent polymer and CR1654 pulp fiber with 16 grams of each material and a theoretical saturated capacity of 608 grams of 0.9% saline. Zoning character of pad basis weight targeted 875 grams per square meter (gsm) from back of crotch to front of pad and 700 gsm in back half of the pad. Density targets were zoned at 0.27 grams per cubic centimeter (g/cc) in front and 0.33 g/cc in back. FIG. 8 shows pad shape in planar direction. The pad was 450 mm long and 120 mm wide in the front, 70 mm wide in the center and 95 mm wide in the back.

This result demonstrates that the method described herein is able to provide a shaped absorbent structure with zoned absorbent mass (i.e., located in a selected region of the structure) that is also thin and exhibits all other aspects of the current invention, as an integral part of a consumer product converting operation. This is a desirable combination, as thin off-line-produced absorbents (i.e., prepared prior to product conversion) are available, but cannot provide zoned absorbency, while conventional on-line absorbent forming methods can zone absorbency but cannot generally provide optimally thin structures.

Liquid Saturated Retention Capacity Test Procedure

Figure 9:
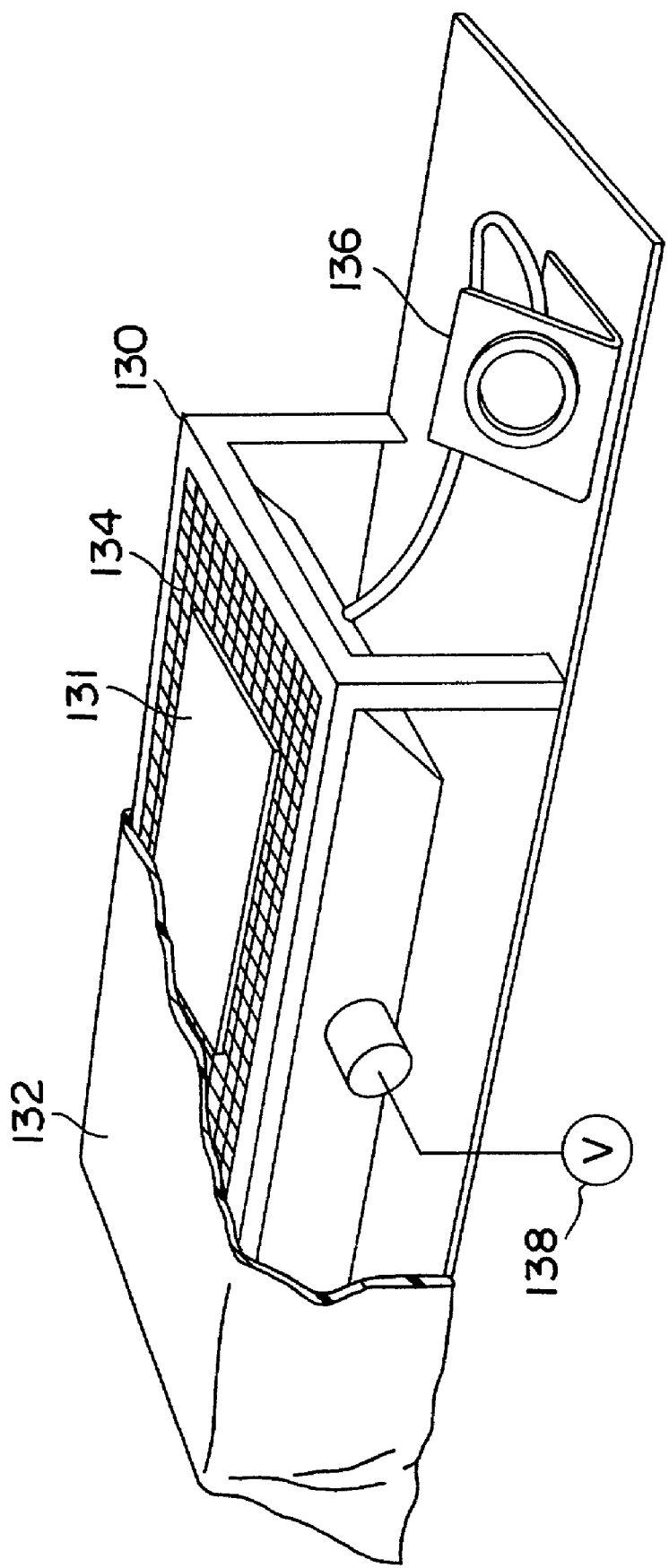
FIG. 9 is an illustration of equipment for determining the liquid saturated retention capacity of an absorbent structure.

The liquid saturated retention capacity is determined as follows. The material to be tested, having a moisture content of less than about 7 weight percent, is weighed and submerged in an excess quantity of a 0.9 weight percent aqueous saline solution at room temperature (about 23 degrees Celsius). The material to be tested is allowed to remain submerged for about 20 minutes. After the 20 minute submerging, the material is removed and, referring to FIG. 9, placed on a TEFLON™ coated fiberglass screen 134 having 0.25 inch (0.6 cm) openings (commercially available from Taconic Plastics Inc., Petersburg, N.Y.) which, in turn, is placed on a vacuum box 130 and covered with a flexible rubber dam material 132. A vacuum of about 0.5 pound per square inch (about 3.5 kilopascals) is drawn on the vacuum box for a period of about 5 minutes with the use of, for example, a vacuum gauge 136 and a vacuum pump 138. The material 131 being tested is then removed from the screen and weighed. The amount of liquid retained by the material being tested is determined by subtracting the dry weight of the material from the wet weight of the material (after application of the vacuum), and is reported as the absolute liquid saturated retention capacity in grams of liquid retained. If desired, the weight of liquid retained may be converted to liquid volume by using the density of the test liquid, and is reported as the liquid saturated retention capacity in milliliters of liquid retained. For relative comparisons, this absolute liquid saturated retention capacity value can be divided by the dry weight of the material 131 to give the specific liquid saturated retention capacity in grams of liquid retained per gram of tested material. If material, such as hydrogel-forming polymeric material or fiber, is drawn through the fiberglass screen 134 while on the vacuum box, a screen having smaller openings should be used. Alternatively, a piece of tea bag or similar material can be placed between the material 131 and the screen 134 and the final value adjusted for the liquid retained by the tea bag or similar material.

Absorbency Under Load (AUL) Test Procedure

Figure 10:
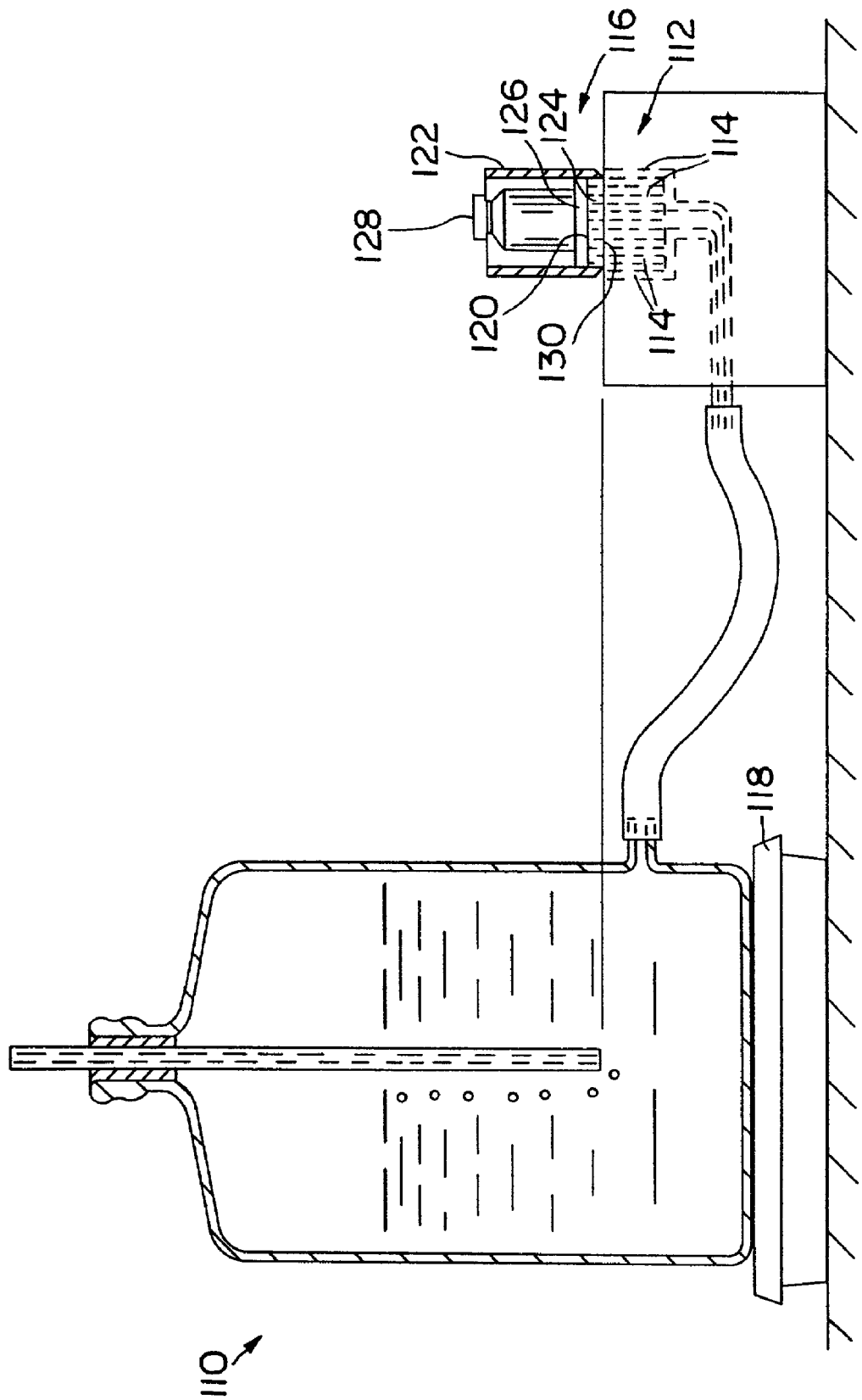
FIG. 10 is an illustration of equipment for determining the Absorbency Under Load (AUL) of superabsorbent material.

The ability of a superabsorbent material to absorb a liquid while under a load is determined as follows. With reference to FIG. 10, a Demand Absorbency Tester (DAT) 110 is used, which is similar to the GATS (Gravimetric Absorbency Test System), available from M/K systems, Danners, Mass., as well as the system described by Lichstein at pages 129-142 of the INDA Technological Symposium Proceedings, March 1974. A porous plate 112 is used, having ports 114 confined within a 2.5 centimeter diameter area and covered by the Absorbency Under Load (AUL) apparatus 116. An electrobalance 118 is used to measure the flow of fluid into the superabsorbent particles 120. For this test, the fluid employed is an aqueous solution containing 0.9 weight percent sodium chloride used at room temperature (approximately 23° Celsius).

The special AUL apparatus 116 used to contain the superabsorbent particles comprises a cylinder 122 made from 1 inch (2.54 centimeters) inside diameter thermoplastic tubing which is machined-out slightly to be sure of concentricity. A 100 mesh stainless steel wire cloth 124 is adhered on the bottom of cylinder 122 by means of an adhesive. Alternatively, the stainless steel wire cloth 124 can be fused to the bottom of cylinder 122 by heating the wire cloth in a flame until red hot, after which the cylinder is held onto the cloth until cooled. A soldering iron can be used to touch up the seal if unsuccessful or if it breaks. Care must be taken to maintain a flat, smooth bottom, and not distort the inside of the cylinder. A 4.4 gram piston 126 is made from 1 inch diameter solid material (e.g. Plexiglass™) and is machined to closely fit without binding in the cylinder 122. The piston 126 is used to provide the restraining load of 0.01 pound per square inch. A weight 128 is used to provide the greater degrees of restraining load. As discussed above, the greater restraining loads are 0.29 pound per square inch, 0.57 pound per square inch, and 0.90 pound per square inch. Accordingly, a 100, 200, and 317 gram weight is used to provide the respective restraining loads (in addition to the 4.4 gram piston 126). A sample of superabsorbent particles weighing 0.160 (±0.005) gram is utilized for testing AUL. The sample is taken from granules which are pre-screened through U.S. standard 30 mesh and retained on U.S. standard 50 mesh (300-600 microns). The particles, when tested, have a moisture content of less than about 5 weight percent.

This test is initiated by placing a 3 centimeter diameter GF/A glass filter paper 130 onto the plate 112. The paper is sized to be larger than the internal diameter and smaller than the outside diameter of the cylinder 122 to ensure good contact while eliminating evaporation over the ports 114 of the DAT 110 and then allowing saturation to occur. The particles 120 are weighed on weighing paper and placed on the wire cloth 124 at the bottom of the AUL apparatus 116. The apparatus 116 is shaken to level the particles 120 on the wire cloth 124. Care is taken to be sure no particles are clinging to the wall of the cylinder 122. After carefully placing, without pressing, the piston 126 and, optionally, weight 128 on the particles 120 in the cylinder 122, the AUL apparatus 116 is placed on the glass filter paper 130. The amount (in grams) of fluid picked up is monitored as a function of time either directly by hand, with a strip-chart recorder, or directly into a data acquisition or personal computer system.

The amount (in grams) of fluid picked up after 60 minutes, divided by the dry weight of the sample (0.160 gram) is the AUL value in grams of fluid picked up per gram of sample (g/g). The rate of fluid picked up can also be measured. Two checks can be made to ensure the accuracy of the instantaneous final readout. First, the height the piston 126 rises, multiplied by the cross-sectional area of the cylinder 122 should equal the volume of fluid picked up. Second, the AUL apparatus 116 can be weighed before and after the test, and the difference in weight should nearly equal the weight of fluid picked up. A minimum of three replicates are performed on a given material and averaged to assign an AUL value.

Edge Compression Test Procedure

The method by which the Edge-wise Compression (EC) value can be determined is set forth below. A 2-inch by 12-inch (5.1 cm by 30.5 cm) piece of absorbent material is cut with its longer dimension aligned with the longitudinal direction of the product or raw material web. The weight of the sample is determined. The thickness of the material is determined under a 0.2 psi (1.38 KA) load. The material is formed into a cylinder having a height of 2 inches (5.1 cm), and with the two ends having 0-0.125 inch (0-3.18 mm) overlap, the material is stapled together with three staples. One staple is near the middle of the width of the product, the other two nearer each edge of the width of the material. The longest dimension of the staple is in the circumference of the formed cylinder to minimize the effect of the staples on the testing.

A tensile tester, such as those commercially available from MTS Systems Corporation, Eden Prairie, Minn., is configured with a bottom platform, a platen larger than the circumference of the sample to be tested and parallel to the bottom platform, attached to a compression load cell placed in the inverted position. The specimen is placed on the platform, under the platen. The platen is brought into contact with the specimen and compresses the sample at a rate of 25 mm/min. The maximum force obtained in compressing the sample to 50% of its width (1 inch) (2.54 cm) is recorded.

If the material buckles, it is typical for the maximum force to be reached before the sample is compressed to 50%. In a product where the length of the absorbent is less than 12 inches (30.5 cm), the EC value of the material can be determined in the following manner. A detailed discussion of the edge-wise compression strength has been given in *The Handbook Of Physical And Mechanical Testing Of Paper And Paperboard*, Richard E. Mark editor, Dekker 1983 (Vol. 1). Based on theoretical models governing buckling stresses, in the Edge-wise Compression configuration described, the buckling stress is proportional to $E*t^2/(H^2)$ with the proportionality constant being a function of $H^2/(R*t)$ where E is the Elastic modulus, H is the height of the cylinder, R is the radius of the cylinder, and t is the thickness of the material. Expressing the stress in terms of force per basis weight, it can be shown that the parameter that needs to be maintained constant is $H^2/R$. Therefore, for a sample that is smaller than 12 inches (30.5 cm), the largest possible circle should be constructed and its height (width of the sample being cut out) adjusted such that $H^2/R$ equals 2.1 inches (5.3 cm).

Bulk and Density Test Procedures

A region of the absorbent pad to be tested is placed under a 0.2 psi weight, and the bulk of the absorbent in this region is recorded. The area under compression should be larger than a 2-inch by 2-inch (5.08 cm by 5.08 cm) square. A suitable tester for absorbent bulk is a Starret-type bulk tester equipped with a 3-inch diameter brass foot that applies a weight of 0.2 psi. The area under compression is marked around the perimeter of the weight while the weight is in place. The weight is removed, and a 2-inch by 2-inch square is cut out from within the outlined region, such as by a die cut. Any tissue present on the absorbent pad is removed, and the square is weighed. The density is determined by the following calculation: density=mass of absorbent in g/(5.08 cm)$^2$×(bulk in cm).

Centrifuge Retention Capacity Test Procedure (CRC Test)

As used herein, the Centrifugal Retention Capacity (CRC) is a measure of the absorbent capacity of the superabsorbent material after being subjected to centrifugation under controlled conditions. The superabsorbent sample to be tested is taken from superabsorbent material which is prescreened through U.S. standard #30 mesh and retained on U.S. standard #50 mesh. The superabsorbent material therefore has a particle size of between 300 and 600 microns. The particles can be prescreened by hand or automatically.

The CRC can be measured by placing 0.200 grams of the sample material to be tested (moisture content of less than 5 weight percent) into a water-permeable bag which will contain the sample while allowing the test solution (0.9 percent NaCl solution) to be freely absorbed by the sample. A heat-sealable tea bag material (grade 542, commercially available from Kimberly-Clark Corporation, Neenah, Wis.) works well for most applications. The bag is formed by folding a 5-inch by 3-inch sample of the bag material in half and heat-sealing two of the open edges to form a 2.5-inch by 3-inch rectangular pouch. The heat seals should be about 0.25 inch inside the edge of the material. After the sample is placed in the pouch, the remaining open edge of the pouch is also heat-sealed. Empty bags are also made to be tested with the sample bags as controls. Three sample bags are tested for each superabsorbent material.

The sealed bags are placed between two TEFLON® coated fiberglass screens having ¼ inch openings (Taconic Plastics, Inc., Petersburg, N.Y.) and submerged in a pan of 0.9 percent NaCl solution at 73.4°±2° Fahrenheit, making sure that the screens are held down until the bags are completely wetted. After wetting, the samples remain in the solution for 30 minutes, at which time they are removed from the solution and temporarily laid on a nonabsorbent flat surface.

The wet bags are then placed into the basket of a suitable centrifuge capable of subjecting the samples to a g-force of 350. (A suitable centrifuge is a Clay Adams Dynac II, model #0103, having a water collection basket, digital rpm gauge, and machined drainage basket adapted to hold and drain the flat bag samples). The samples must be placed in opposing positions within the centrifuge to balance the basket when spinning. The bags are centrifuged at a target of 1600 rpm, but within the range of 1500-1900 rpm, for 3 minutes (target g-force of 350). The bags are removed and weighed, with the empty bags (controls) being weighed first, followed by the bags containing superabsorbent material. The amount of fluid absorbed and retained by the superabsorbent material, taking into account the fluid retained by the bag material alone, is the Centrifugal Retention Capacity of the superabsorbent material, expressed as grams of fluid per gram of superabsorbent material.

Superabsorbent Gel Bed Permeability Test

Figure 11:
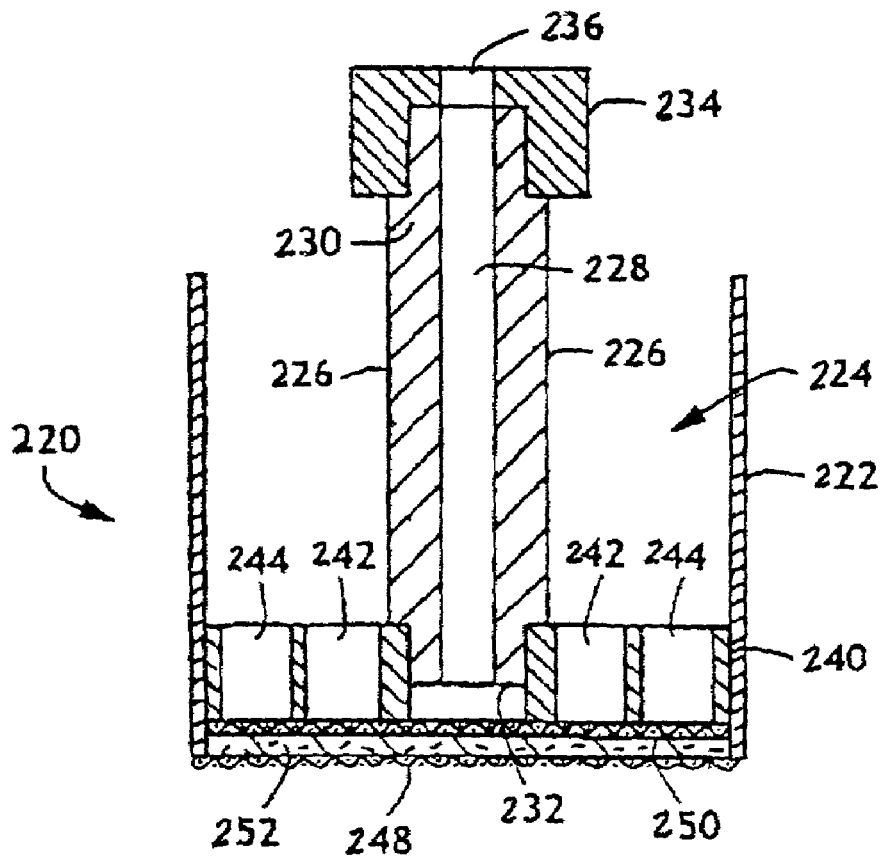
FIGS. 11 and 12 are illustrations of equipment for determining the Superabsorbent Gel Bed Permeability (GBP).
Figure 12:
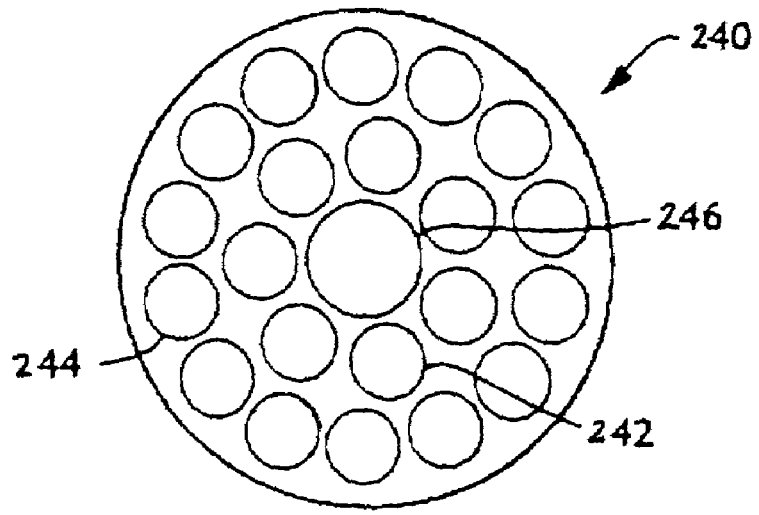

A suitable piston/cylinder apparatus for performing the Gel Bed Permeability (GBP) test is shown in FIGS. 11 and 12. Referring to FIG. 11, an apparatus 220 consists of a cylinder 222 and a piston (generally indicated as 224). As shown in FIG. 11, the piston 224 consists of a cylindrical LEXAN shaft 226 having a concentric cylindrical hole 228 bored down the longitudinal axis of the shaft. Both ends of the shaft 226 are machined to provide first and second ends 230, 232. A weight 234 rests on the first end 230 and has a cylindrical hole 236 bored through the center thereof. Inserted on the second end 232 is a circular piston head 240. The piston head 240 is sized so as to vertically move inside the cylinder 222.

As shown in FIG. 12, the piston head 240 is provided with inner and outer concentric rings containing seven and fourteen approximately 0.375 inch (0.95 cm) cylindrical holes, respectively (indicated generally by arrows 242 and 244). The holes in each of these concentric rings are bored from the top to bottom of the piston head 240. The piston head 240 also has a cylindrical hole 246 bored in the center thereof to receive the second end 232 of the shaft 226.

Attached to the bottom end of the cylinder 222 is a No. 400 mesh stainless steel cloth screen 248 that is biaxially stretched to a tautness prior to attachment. Attached to the bottom end of the piston head 240 is a No. 400 mesh stainless steel cloth screen 250 that is biaxially stretched to a tautness prior to attachment. A sample of adsorbent material 252 is supported on the screen 248.

The cylinder 222 is bored from a transparent LEXAN rod or equivalent and has an inner diameter of 6.00 cm (area=28.27 cm$^2$), a wall thickness of approximately 0.5 cm, and a height of approximately 5.0 cm. The piston head 240 is machined from a LEXAN rod. It has a height of approximately 0.625 inches (1.59 cm) and a diameter sized such that it fits within the cylinder 222 with minimum wall clearances, but still slides freely. A hole 246 in the center of the piston head 240 has a threaded 0.625 inch (1.59 cm) opening (18 threads/inch) for the second end 232 of the shaft 226.

The shaft 226 is machined from a LEXAN rod and has an outer diameter of 0.875 inches (2.22 cm) and an inner diameter of 0.250 inches (0.64 cm). The second end 232 is approximately 0.5 inches (1.27 cm) long and is threaded to match the hole 246 in the piston head 240. The first end 230 is approximately 1 inch (2.54 cm) long and 0.623 inches (1.58 cm) in diameter, forming an annular shoulder to support the stainless steel weight 234.

The annular stainless steel weight 234 has an inner diameter of 0.625 inches (1.59 cm), so that it slips onto the first end 230 of the shaft 226 and rests on the annular shoulder formed therein. The combined weight of the piston 224 and the weight 134 equals approximately 596 g, which corresponds to a pressure of 0.30 psi (20,685 dynes/cm), for an area of 28.27 cm$^2$. When fluids flow through the piston/cylinder apparatus, the cylinder 222 generally rests on a 16-mesh, rigid stainless-steel support screen (not shown) or equivalent.

The piston and weight are placed in an empty cylinder to obtain a measurement from the bottom of the weight to the top of the cylinder. This measurement is taken using a caliper readable to 0.01 mm. This measurement will later be used to calculate the height of the bed of the sample of adsorbent material 252. It is important to measure each cylinder empty and keep track of which piston and weight were used. The same piston and weight should be used for measurement when the sample of adsorbent material is swollen.

The adsorbent layer used for GBP measurements is formed by swelling approximately 0.9 g of a sample of adsorbent material in the GBP cylinder apparatus (dry adsorbent material should be spread evenly over the screen of the cylinder prior to swelling) with a fluid, typically 0.9% (w/v) aqueous NaCl, for a time period of approximately 15 minutes. The sample of adsorbent material is taken from a population of adsorbent material that is prescreened through U.S. standard 30 mesh and retained on U.S. standard 50 mesh. The adsorbent material, therefore, has a particle size of between 300 and 600 microns. The particles may be prescreened by hand or automatically prescreened with, for example, a Ro-Tap Mechanical Sieve Shaker Model B, commercially available from W.S. Tyler, Inc., Mentor, Ohio, USA.

At the end of the 15 minute period, the cylinder is removed from the fluid and the piston/weight assembly is placed on the sample of adsorbent material. The thickness of the swollen sample of adsorbent material is determined by measuring from the bottom of the weight to top of the cylinder with a micrometer. The value obtained when taking this measurement with the empty cylinder is subtracted from the value obtained after swelling the sample of adsorbent material. The resulting value is the height of the bed of the swollen sample of adsorbent material, H.

The GBP measurement is initiated by adding the fluid to the cylinder 222 until the fluid attains a height of 4.0 cm above the bottom of the sample of adsorbent material 252. This fluid height is maintained throughout the test. The quantity of fluid passing through the sample of adsorbent material 252 versus time is measured gravimetrically. Data points are collected every second for the first two minutes of the test and every two seconds for the remainder. When the data are plotted as quantity of fluid passing through the bed of the sample of adsorbent material versus time, it becomes clear to one skilled in the art when a steady flow rate has been attained.

Only data collected once the flow rate has become steady is used in the flow rate calculation. The flow rate, Q, through the sample of adsorbent material 252, is determined in units of g/s by a linear least-square fit of fluid passing through the sample of adsorbent material (in grams) versus time (in seconds). Permeability in cm$^2$ is obtained by the following equation: $K=[Q*(H*\mu)]/[A*\rho*P]$, where K=Gel Bed Permeability (cm$^2$); Q=flow rate (g/sec); H=height of bed of sample of adsorbent material (cm); μ=liquid viscosity (poise); A=cross-sectional area for liquid flow (cm$^2$); ρ=liquid density (g/cm3); and P=hydrostatic pressure (dynes/cm$^2$) (normally approximately 3,923 dynes/cm$^2$).

It will be appreciated that details of the foregoing embodiments, given for purposes of illustration, are not to be construed as limiting the scope of this invention. Although only a few exemplary embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention, which is defined in the following claims and all equivalents thereto. Further, it is recognized that many embodiments may be conceived that do not achieve all of the advantages of some embodiments, particularly of the preferred embodiments, yet the absence of a particular advantage shall not be construed to necessarily mean that such an embodiment is outside the scope of the present invention.

We claim:
1. An absorbent pad, comprising:
   a single, densified layer including between 30 and 85 wt % superabsorbent material homogeneously mixed with between 15 and 70 wt % pulp fluff;
   wherein the single-layer absorbent pad has been compacted to a density greater than about 0.28 grams per cubic centimeter and a thickness in a range of between 0.5 and 3.0 millimeters, and the single-layer absorbent pad also has an absorbent capacity between about 14 and 40 grams 0.9 w/v % saline solution per gram of absorbent pad and an edge compression between about 2726 and about 3615 gm-cm of energy to 50% compression.
2. The absorbent pad of claim 1, wherein the absorbent pad has a density greater than about 0.30 grams per cubic centimeter.

3. The absorbent pad of claim 1, wherein the absorbent pad has a density greater than about 0.32 grams per cubic centimeter.

4. The absorbent pad of claim 1, wherein the absorbent pad comprises between 40 and 80 wt % superabsorbent material.

5. The absorbent pad of claim 1, wherein the absorbent pad comprises between 50 and 75 wt % superabsorbent material.

6. The absorbent pad of claim 1, further comprising a plurality of man-made fibers.

7. The absorbent pad of claim 1, further comprising a plurality of carrier particles.

8. The absorbent pad of claim 1, wherein the absorbent pad is between 0.6 and 2.5 millimeters thick.

9. The absorbent pad of claim 1, wherein the absorbent pad is between 0.7 and 2.0 millimeters thick.

10. The absorbent pad of claim 1, wherein the absorbent pad has an absorbent saturation capacity between 16 and 40 grams 0.9 w/v % saline solution per gram of absorbent pad.

11. The absorbent pad of claim 1, wherein the absorbent pad has an absorbent saturation capacity between 18 and 40 grams 0.9 w/v % saline solution per gram of absorbent pad.

12. The absorbent pad of claim 1, wherein the superabsorbent material has a gel strength of at least 0.65.

13. The absorbent pad of claim 1, wherein the superabsorbent material has a gel strength of at least 0.75.

14. The absorbent pad of claim 1, wherein the superabsorbent material has a gel strength of at least 0.85.

15. An absorbent article comprising the absorbent pad of claim 1.

16. A diaper comprising the absorbent pad of claim 1.

17. A training pant comprising the absorbent pad of claim 1.

18. A feminine hygiene product comprising the absorbent pad of claim 1.

19. An incontinence product comprising the absorbent pad of claim 1.

20. A swim wear garment comprising the absorbent pad of claim 1.

21. The absorbent pad of claim 1, wherein the absorbent pad has a higher basis weight in a first zone than in a second zone.

22. The absorbent pad of claim 1, further comprising a wrap material encompassing the single-layer absorbent pad.

23. The absorbent pad of claim 1, wherein the single-layer absorbent pad is formed to a specific shape.

24. An absorbent pad, comprising:
a single, densified layer including between 30 and 85 wt % superabsorbent material; and
between 15 and 70 wt % pulp fluff
wherein the single-layer absorbent pad has been compacted to a density greater than about 0.30 grams per cubic centimeter and a thickness in a range of between 0.5 and 3.0 millimeters, and the single-layer absorbent pad also has an edge compression between about 2726 and about 3615 gm-cm of energy to 50% compression, and the superabsorbent material forms a gradient within the absorbent pad.

25. The absorbent pad of claim 24, wherein the absorbent pad comprises between 40 and 80 wt % superabsorbent material.

26. The absorbent pad of claim 24, wherein the absorbent pad comprises between 50 and 75 wt % superabsorbent material.

27. The absorbent pad of claim 24, further comprising a plurality of man-made fibers.

28. The absorbent pad of claim 24, further comprising a plurality of carrier particles.

29. The absorbent pad of claim 24, wherein the absorbent pad is between 0.6 and 2.5 millimeters thick.

30. The absorbent pad of claim 24, wherein the absorbent pad is between 0.7 and 2.0 millimeters thick.

31. The absorbent pad of claim 24, wherein the absorbent pad has an absorbent saturation capacity between about 14 and 40 grams 0.9 w/v % saline solution per gram of absorbent pad.

32. The absorbent pad of claim 24, wherein the absorbent pad has an absorbent saturation capacity of at least 16 grams 0.9 w/v % saline solution per gram of absorbent pad.

33. The absorbent pad of claim 24, wherein the absorbent pad has an absorbent saturation capacity of at least 18 grams 0.9 w/v % saline solution per gram of absorbent pad.

34. The absorbent pad of claim 24, wherein the superabsorbent material has a gel strength of at least 0.65.

35. The absorbent pad of claim 24, wherein the superabsorbent material has a gel strength of at least 0.75.

36. The absorbent pad of claim 24, wherein the superabsorbent material has a gel strength of at least 0.85.

37. The absorbent pad of claim 24, wherein the absorbent pad includes more superabsorbent material at a first end than at a second end opposite the first end.

38. The absorbent pad of claim 24, wherein the absorbent pad includes more superabsorbent material along a top surface than along a bottom surface.

39. The absorbent pad of claim 24, wherein the absorbent pad includes more superabsorbent material along a bottom surface than along a top surface.

40. The absorbent pad of claim 24, wherein a concentration of the superabsorbent material varies throughout the gradient by about 0.01 to about 0.40 grams per cubic centimeter.

41. The absorbent pad of claim 24, wherein a concentration of the superabsorbent material varies throughout the gradient by about 0.05 to about 0.35 grams per cubic centimeter.

42. The absorbent pad of claim 24, wherein a concentration of the superabsorbent material varies throughout the gradient by about 0.15 to about 0.25 grams per cubic centimeter.

43. The absorbent pad of claim 24, further comprising a wrap material encompassing the single-layer absorbent pad.

44. The absorbent pad of claim 24, wherein the single-layer absorbent pad is formed to a specific shape.

* * * * *